(12) United States Patent
Kusuda et al.

(10) Patent No.: US 7,560,475 B2
(45) Date of Patent: Jul. 14, 2009

(54) PHENYLACETIC ACID DERIVATIVE, PROCESS FOR PRODUCING THE SAME, AND USE

(75) Inventors: Shinya Kusuda, Mishima-gun (JP); Yoshisuke Nakayama, Mishima-gun (JP); Hisao Tajima, Mishima-gun (JP); Takahiko Sakamoto, Sakai-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 264 days.

(21) Appl. No.: 10/572,937

(22) PCT Filed: Sep. 21, 2004

(86) PCT No.: PCT/JP2004/014137

§ 371 (c)(1),
(2), (4) Date: Mar. 22, 2006

(87) PCT Pub. No.: WO2005/028453

PCT Pub. Date: Mar. 31, 2005

(65) Prior Publication Data

US 2007/0105868 A1    May 10, 2007

(30) Foreign Application Priority Data

Sep. 22, 2003  (JP) .............................. 2003-330616
Aug. 6, 2004   (JP) .............................. 2004-231546

(51) Int. Cl.
| | | |
|---|---|---|
| A01N 31/425 | (2006.01) | |
| A01N 43/50  | (2006.01) | |
| A01N 43/76  | (2006.01) | |
| A01N 43/78  | (2006.01) | |
| A61K 31/42  | (2006.01) | |
| A61K 31/415 | (2006.01) | |
| C07D 233/54 | (2006.01) | |
| C07D 263/30 | (2006.01) | |
| C07D 277/22 | (2006.01) | |
| C07D 413/00 | (2006.01) | |

(52) U.S. Cl. .................. 514/365; 514/374; 514/396; 548/203; 548/235; 548/341.1

(58) Field of Classification Search ................ 548/203, 548/235, 341.1; 514/365, 374, 396
See application file for complete search history.

(56) References Cited

FOREIGN PATENT DOCUMENTS

| | | |
|---|---|---|
| JP | 2002-265457 A | 9/2002 |
| WO | WO 99/46232 A1 | 9/1999 |
| WO | WO 01/16120   * | 3/2001 |
| WO | WO 02/096358  * | 12/2002 |
| WO | WO 03/072102 A1 | 9/2003 |
| WO | WO 03/721000 A1 | 9/2003 |

OTHER PUBLICATIONS

West, Anthony R., Solid State Chemistry and its Applications, Wiley, New York, 1988, pp. 358 & 365.*
Wolff, Manfred E. "Burger's Medicinal Chemistry, 5ed, Part I", John Wiley & Sons, 1995, pp. 975-977.*
Banker, G.S., et al, Modern Pharmaceutics, 3ed., Marcel Dekker, New York, pp. 451 & 596 (1996).*
Vosper, et al., Peroxisome proliferator-activated receptor agonists, hyperlipidaemia, and atherosclerosis, Pharmacology & Therapeutics, vol. 95, pp. 47-62 (2002).*

* cited by examiner

Primary Examiner—James O Wilson
Assistant Examiner—Erich A Leeser
(74) Attorney, Agent, or Firm—Sughrue Mion, PLLC

(57) ABSTRACT

The present invention relates to the compound represented by formula (I)

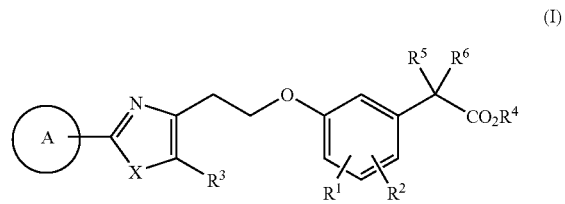

(wherein $R^1$ and $R^2$ is hydrogen atom, C1-8 alkyl etc.; $R^3$ is C1-8 alkyl which may be substituted with 1 to 3 halogen atom(s), phenyl; $R^4$ is hydrogen atom etc.; $R^5$ and $R^6$ is hydrogen atom, C1-8 alkyl etc.; X is sulfur atom or oxygen atom etc.; ringA is cyclic group which may have a substituent(s).), or a salt thereof. Toxicity of the compound represented by formula (I) is very low, and it is safe enough to use as a pharmaceutical agent and since it has PPAR δ agonistic activity, it is useful as preventive and/or therapeutic agent for glucose•lipid metabolic disorder, hypertension, circulatory diseases etc.

8 Claims, No Drawings

000# PHENYLACETIC ACID DERIVATIVE, PROCESS FOR PRODUCING THE SAME, AND USE

TECHNICAL FIELD

The present invention relates to phenylacetic acid derivatives useful for therapy for hyperlipidemia etc., preparations thereof and use thereof.

BACKGROUND ART

Recently in the study of transcription factors associated with marker genes expression induction in adipocytes differentiation, peroxisome proliferator activated receptor (abbreviated as PPAR hereinafter), which is one of intranuclear receptors, has got attention. The cDNAs of PPAR were cloned from various kinds of animals, and plural isoform genes were found, particularly in mammals three types of isoforms ($\alpha$, $\delta$, $\gamma$) are known (see *J Steroid Biochem. Molec. Biol.*, 51, 157 (1994); *Gene Expression.*, 4, 281 (1995); *Biochem Biophys. Res. Commun.*, 224, 431 (1996); *Mol. Endocrinology.*, 6, 1634 (1992)). Further, it is known that PPAR $\gamma$ isoform predominantly expresses in adipose tissues, immune cells, adrenal gland, spleen, small intestine, PPAR $\alpha$ isoform mainly expresses in adipose tissue, liver, retina, and PPAR $\delta$ isoform universally expresses without specificity for tissue (see *Endocrinology.*, 137, 354 (1996)).

By the way, thiazolidine derivatives such as pioglitazone, ciglitazone, rosiglitazone, troglitazone etc. are known as agents for the treatment of non-insulin dependent diabetes mellitus (NIDDM) and are hypoglycemic agents which are used for the improvement of hyperglycemia in the patients suffering from diabetes. They are also effective for the improvement or correction of hyperinsulinemia, improvement of glucose tolerance and decrease of serum lipid and therefore they are thought to be considerably hopeful as agents for the improvement of insulin resistance.

In addition, one of the intracellular target proteins of these thiazolidine derivatives is exactly PPAR $\gamma$ and it is resolved that they enhance the transcription activity of PPAR $\gamma$ (see *Endocrinology.*, 137, 4189 (1996); *Cell.*, 83, 803 (1995); *Cell.*, 83, 813 (1995); *J. Biol. Chem.*, 270, 12953 (1995)). Therefore, a PPAR $\gamma$ activator (agonist) which enhances its transcription activity is thought to be hopeful as a hypoglycemic agent and/or a hypolipidemic agent. Furthermore, since a PPAR $\gamma$ agonist is known to promote the expression of PPAR $\gamma$ protein itself (*Genes & Development.*, 10, 974 (1996)), an agent which increases the expression of PPAR $\gamma$ protein itself as well as PPAR $\gamma$ activating agent is also thought to be clinically useful. Intracellular receptor, PPAR $\gamma$ is related to adipocytes differentiation (see *J. Biol. Chem.*, 272, 5637 (1997) and *Cell.*, 83, 803 (1995)). It is known that thiazolidine derivatives which activate this receptor promote adipocytes differentiation. Recently it was reported that thiazolidine derivatives increase body fat and cause man to gain weight and to become obese (see *Lancet.*, 349, 952 (1997)). From these, PPAR $\gamma$ activators (agonists) and PPAR $\gamma$ regulators for its expression that can increase the expression of the protein itself have hypoglycemic effect, hypolipidemic effect and are expected to be useful as agents for prevention and/or treatment of such as, glucose•lipid metabolic disorder (e.g. diabetes, hyperlipidemia (hypercholesterolemia, hypo-HDL (high-density lipoprotein)-cholesterolemia, hyper-LDL (low-density lipoprotein)-cholesterolemia, hypertriglyceridemia etc.), atherosclerosis, cardiovascular disease, hypertension, circulatory diseases etc.

Additionally, the fibrate compound (e.g., chlofibrate) is known as a hypolipidemic agent. It is also resolved that one of the intracellular target proteins of fibrate compounds is PPAR $\alpha$ (see *Nature.*, 347, 645 (1990); *J. Steroid Biochem. Molec. Biol.*, 51, 157 (1994); *Biochemistry.*, 32, 5598 (1993)). From these facts, PPAR $\alpha$ regulators are thought to have a hypolipidemic effect, and so they are expected to be useful as agents for prevention and/or treatment of hyperlipidemia etc.

Besides, it has been recently reported that PPAR $\alpha$ possesses anti-obese activity (see WO97/36579). In addition, it was reported that the metabolic stimulation effect of lipid (cholesterol, HDL, LDL and triglyceride etc.) were induced by PPAR $\alpha$ agonists (see *J. Lipid Res.*, 39, 17 (1998)). That is, it was reported that they had the elevating effect of high-density lipoprotein (HDL) cholesterol and the lowering effect of low-density lipoprotein (LDL) cholesterol, very low-density lipoprotein (VLDL) cholesterol and triglyceride. It was also reported that composition of fatty acids in blood, hypertension and insulin resistance were improved by administration of bezafibrate which is one of fibrate compounds (see *Diabetes.*, 46, 348 (1997)). Therefore, since agonists that activate PPAR $\alpha$ and PPAR $\alpha$ regulators that promote expression of PPAR $\alpha$ protein itself have hypolipidemic effect, they are hopeful agents for the treatment and/or prevention of lipid metabolic disorder (e.g. hyperlipidemia (hypercholesterolemia, hypo-HDL-cholesterolemia, hyper-LDL-cholesterolemia, hypertriglyceridemia etc.), atherosclerosis, cardiovascular disease, adiposity, metabolic syndrome etc.), hypertension, circulatory diseases etc.

In contrast, PPAR $\delta$ is sometimes called PPAR $\beta$, or it is also called NUC1 in human. Until now, as for activity of PPAR $\delta$, it is disclosed that hNUC1B (PPAR subtype whose structure is different from that of human NUC1 in one amino acid) inhibited the transcription activities of human PPAR $\alpha$ and thyroid hormone receptor (see WO9604130). Recently, it was reported that the compounds, which possessed high affinity to PPAR $\delta$ protein and which could activate PPAR $\delta$ significantly (i.e. agonists) were found out and that they had HDL (high density lipoprotein) cholesterol level-elevating activity and non-HDL cholesterol level-lowering effect (see WO9728149, WO0100603, *Proc. Natl. Acad. Sci. USA.*, 98, 5306 (2001)). It turned out that macrophages introduced oxidized LDL, their foam occurred and they deposited into vascular endothelium to cause lipid metabolic disease. Therefore, agonists that can activate PPAR $\delta$ reduce foam cells by HDL cholesterol level-elevating effect and LDL cholesterol level-lowering effect and so they are expected to be useful for preventive and/or therapeutic agent of lipid metabolic disorder (e.g. hyperlipidemia (hypercholesterolemia, hypo-HDL-cholesterolemia, hyper-LDL-cholesterolemia, hypertriglyceridemia etc.), atherosclerosis, cardiovascular disease, adiposity, metabolic syndrome etc.), hypertension, circulatory diseases etc.

Recently, it was reported that activation of PPAR $\delta$ increased fatty acid oxidation in especially skeletal muscles (see *Proc. Natl. Acad. Sci. USA.*, 100, 15924 (2003)). This also suggests that PPAR $\delta$ agonists are useful for the improvement of lipid metabolic disorder and therapy of adiposity.

The activation of PPAR $\delta$ doesn't only have the effect on lipid metabolic disorder, but also promote the cell differentiation of keratinocytes and is involved in sustain of skin structure as barrier function of organisms. It is observed that the over-proliferative changes of skins occur in PPAR $\delta$-deficient mice treated with TPA (12-O-tetradecanoylphorbol-13-acetate) (see *Mol. Cell. Biol.*, 20, 5119 (2000)). In addition, it is shown that it has the anti-inflammatory activity on dermal inflammation (see *J. Invest. Dermatol.*, 122, 971

(2004)). Therefore, PPAR δ agonists are useful for the preventive and/or therapeutic agent of dermal inflammatory disease (e.g. dermatitis (atopic dermatitis etc.), erythralgia, pruritus etc.) and are expected to have the effect as therapeutic facilitated drug of wound (e.g. burn wound, external wound etc.). Additionally, it is observed that callosal myelin coating disorder occurs in PPAR δ-deficient mice (see *Mol. Cell. Biol.*, 20, 5119 (2000)) and PPAR δ agonists have possibility of having utility as preventive and/or therapeutic agent of a certain nerve disease.

However, it was reported that certain drugs among PPAR γ agonists had hepatopathy and they required careful use as medicine. In addition, it is speculated that hepatotoxicity of side effect derives from thiazolidine structure, but there are no reports which any structure of compounds concretely avoids hepatotoxicity. It is very useful that they search structure able to avoiding toxicity on developing PPAR agonists.

In contrast, the compounds represented by formula (A)

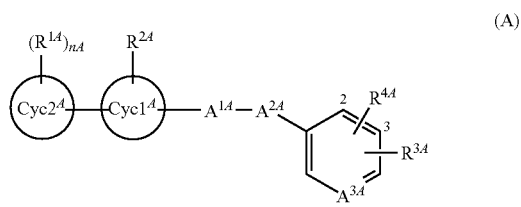

(wherein $A^{1A}$ is C1-4 alkylene etc.; $A^{2A}$ is —O—; $A^{3A}$ is CH etc.; nA is 1 to 5; $R^{1A}$ is a halogen atom, trihalomethyl, trihalomethoxy etc.; $R^{2A}$ is C1-4 alkyl, trihalomethyl etc.; Cyc1$^A$ is 1,3-thiazolilene, 1,3-oxazolilene etc.; Cyc2$^A$ is carbocyclic ring, heterocyclic ring etc.; $R^{3A}$ is a hydrogen atom, C1-8 alkyl etc.; $R^{4A}$ is -$A^{4A}$—$CR^{8A}R^{9A}$—$COOR^{7A}$ (wherein $A^{4A}$ is a single bond; $R^{7A}$, $R^{8A}$, $R^{9A}$ is a hydrogen atom, C1-4 alkyl) etc.) are known to be useful as PPAR regulator (see WO9946232).

DISCLOSURE OF THE INVENTION

The problem of the present invention is in developing safe PPAR agonists which are useful for preventive and/or therapeutic agent of hyperlipidemia etc. and have reduced side effects.

Referring the above-mentioned problem, as a result of the present inventors made further investigation to find out that the compounds represented below by formula (I) among the compounds represented by the above-described formula (A) have extremely low toxicity, that especially they can avoid hepatotoxicity and the complete the present invention.

That is, the present invention relates to the followings:

1. A compound represented by formula (I)

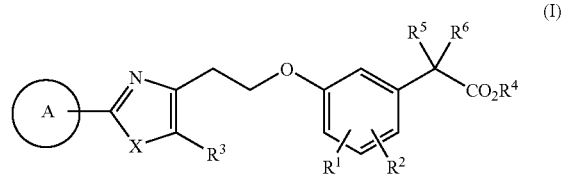

wherein $R^1$ and $R^2$ each independently represents a hydrogen atom, C1-8 alkyl, halogen atom, C1-4 alkoxy, nitro, trihalomethyl, trihalomethoxy, trihalomethylthio, cyano, C1-4 alkylthio or $NR^7R^8$, in which $R^7$ and $R^8$ each independently represents a hydrogen atom, or C1-4 alkyl); $R^3$ represents C1-8 alkyl which may be substituted with a 1-3 halogen atom(s) or phenyl; $R^4$ represents a hydrogen atom or C1-8 alkyl; $R^5$ and $R^6$ each independently represents a hydrogen atom or C1-4 alkyl, or $R^5$ and $R^6$ may be together with their neighboring carbon atom to form a carbocyclic ring; X represents a sulfur atom, an oxygen atom or a nitrogen atom which may have a substituent(s); ringA represents a cyclic group which may have a substituent(s), a salt thereof, or a solvate thereof or a prodrug thereof.

2. The compound according to the above-described 1, wherein the cyclic group represented by ringA is 4-(trifluoromethyl)phenyl, 4-(trifluoromethoxy)phenyl, 4-(trifluoromethyl)piperidin-1-yl, 2,2-difluoro-1,3-benzodioxol-5-yl, 4-phenylpiperidin-1-yl, 4-phenylpiperazin-1-yl, 1,3-dihydro-2H-isoindole-2-yl, 4-(4-chlorophenyl)piperazin-1-yl or 3,4-dihydro-1H-isoquinolin-2-yl, 3. The compound according to the above-described 2, wherein the cyclic group represented by ringA is 4-(trifluoromethyl)piperidin-1-yl, 2,2-difluoro-1,3-benzodioxol-5-yl or 3,4-dihydro-1H-isoquinolin-2-yl, 4. The compound according to the above-described 1, wherein the compound is
(1) [3-(2-{5-methyl-2-[4-(trifluoromethyl)piperidin-1-yl]-1,3-thiazol-4-yl}ethoxy)phenyl]acetic acid,
(2) [3-(2-{5-isopropyl-2-[4-(trifluoromethyl)phenyl]-1,3-oxazol-4-yl}ethoxy)-4-methylphenyl]acetic acid,
(3) [3-(2-{5-ethyl-2-[4-(trifluoromethyl)piperidin-1-yl]-1,3-thiazol-4-yl}ethoxy)-4-methylphenyl]acetic acid,
(4) [3-(2-{5-isopropyl-2-[4-(trifluoromethoxy)phenyl]-1,3-oxazol-4-yl}ethoxy)-4-methylphenyl]acetic acid,
(5) (3-{2-[2-(2,2-difluoro-1,3-benzodioxol-5-yl)-5-isopropyl-1,3-oxazol-4-yl]ethoxy}-4-methylphenyl)acetic acid,
(6) [3-(2-{5-ethyl-2-[4-(trifluoromethoxy)phenyl]-1,3-oxazol-4-yl}ethoxy)-4-methylphenyl]acetic acid,
(7) (3-{2-[2-(2,2-difluoro-1,3-benzodioxol-5-yl)-5-methyl-1,3-oxazol-4-yl]ethoxy}-4-methylphenyl)acetic acid,
(8) [2-fluoro-3-(2-{5-methyl-2-[4-(trifluoromethyl)piperidin-1-yl]-1,3-thiazol-4-yl}ethoxy)phenyl]acetic acid,
(9) (2-fluoro-3-{2-[5-methyl-2-(4-phenylpiperidin-1-yl)-1,3-thizaol-4-yl]ethoxy}phenyl)acetic acid,
(10) (3-{2-[5-methyl-2-(4-phenylpiperazin-1-yl)-1,3-thiazol-4-yl]ethoxy}phenyl)acetic acid,
(11) (3-{2-[2-(1,3-dihydro-2H-isoindole-2-yl)-5-methyl-1,3-thiazol-4-yl]ethoxy}-2-fluorophenyl)acetic acid,
(12) [3-(2-{2-[4-(4-chlorophenyl)piperazin-1-yl]-5-methyl-1,3-thiazol-4-yl}ethoxy)-2-fluorophenyl]acetic acid or
(13) (3-{2-[2-(3,4-dihydro-1H-isoquinolin-2-yl)-5-methyl-1,3-thiazol-4-yl]ethoxy}-4-methylphenyl)acetic acid, 5. A pharmaceutical composition comprising the compound represented by formula (I) according to the above-described 1, a salt thereof, or a solvent thereof or a prodrug thereof, 6. The pharmaceutical composition according to the above-described 5, wherein the pharmaceutical composition is a preventive and/or therapeutic agent for a PPAR-mediated disease, 7. The pharmaceutical composition according to the above-described 6, wherein PPAR is PPAR δ, 8. The pharmaceutical composition according to the above-described 7, wherein PPAR δ-mediated disease is hyperlipidemia or adiposity, 9. A medicament comprising the compound represented by formula (I) according to the above-described 1, a salt thereof, or a solvent thereof or a prodrug thereof and one or more kinds selected from a MTP inhibitor, a HMG-CoA reductase inhibitor, a squalene synthase inhibitor, a fibrate drug, an ACAT inhibitor, a 5-lipoxygenase inhibitor, a cholesterol absorption inhibitor, a bile acid absorption inhibitor, a Na$^+$/bile acid transporter inhibitor, LDL receptor activator, LDL receptor expression enhancer, a pancreatic lipase inhibitor, a probucol formulation, a nicotine acid formulation and a cholesterol ester transporter protein inhibitor, 10. A method for prevention and/or treatment for PPAR-mediated disease in a mammal, which comprises administering to a mammal an effective amount of a compound represented by formula (I) according to the above-described 1, a salt thereof, or a solvent thereof or a prodrug thereof, and 11. Use of a compound represented by formula (I) according to the above-described 1, a salt thereof, or a solvent thereof or a prodrug thereof for preparing a preventive and/or therapeutic agent for PPAR-mediated disease.

C1-8 alkyl represented by $R^1$, $R^2$ and $R^4$ means straight-chain and branched-chain alkyl, for example methyl, ethyl, n-propyl, isopropyl, n-butyl, isobutyl, sec-butyl, tert-butyl, pentyl, hexyl, heptyl, octyl etc.

Halogen atom represented by $R^1$ and $R^2$ means fluorine, chlorine, bromine, iodine.

C1-4 alkoxy represented by $R^1$ and $R^2$ means straight-chain and branched-chain alkoxy, for example methoxy, ethoxy, n-propoxy, isopropoxy, n-butoxy, isobutoxy, sec-butoxy, tert-butoxy etc.

Trihalomethyl represented by $R^1$ and $R^2$ means methyl tri-substituted with, for example iodine atom(s), bromine atom(s), fluorine atom(s) or chlorine atom(s).

Trihalomethoxy represented by $R^1$ and $R^2$ means methoxy tri-substituted with, for example iodine atom(s), bromine atom(s), fluorine atom(s) or chlorine atom(s).

Trihalomethylthio represented by $R^1$ and $R^2$ means methylthio tri-substituted with, for example iodine atom(s), bromine atom(s), fluorine atom(s) or chlorine atom(s).

C1-4 alkylthio represented by $R^1$ and $R^2$ means straight-chain and branched-chain alkylthio, for example methylthio, ethylthio, n-propylthio, isopropylthio, n-butylthio, isobutylthio, sec-butylthio, tert-butylthio etc.

C1-4 alkyl represented by $R^5$, $R^6$, $R^7$ and $R^8$ means straight-chain and branched-chain alkyl, for example methyl, ethyl, n-propyl, isopropyl, n-butyl, isobutyl, sec-butyl, tert-butyl etc.

"C1-8 alkyl" in the "C1-8 alkyl which may which may be substituted with a 1-3 halogen atom(s)" represented by $R^3$ means straight-chain and branched-chain alkyl, for example methyl, ethyl, n-propyl, isopropyl, n-butyl, isobutyl, sec-butyl, tert-butyl, pentyl, hexyl, heptyl, octyl etc.

Halogen atom in the "C1-8 alkyl which may which may be substituted with a 1-3 halogen atom(s)" means fluorine, chlorine, bromine, iodine.

Carbocyclic ring which $R^5$ and $R^6$ may be together with their neighboring carbon atom to form means, for example C3-10 saturated carbocyclic ring etc. C3-10 saturated carbocyclic ring means, for example cyclopropane, cyclobutane, cycloheptane, cyclohexane, cycloheptane, cyclooctane, cyclononane, cyclodecane, cyclopentene, cyclohexene, cyclopentadiene, cyclohexadiene etc.

"Cyclic group" in the "cyclic group which may have a substituent(s)" represented by ringA means, for example carbocyclic ring or heterocyclic ring etc. Carbocyclic ring means, for example, C3-15 mono-, bi-, or tri-aromatic carbocyclic ring and bridged carbocyclic ring and bridged carbocyclic ring etc. C3-15 mono-, bi-, or tri-aromatic carbocyclic ring and bridged carbocyclic ring means, for example cyclopropane, cyclobutane, cyclopentane, cyclohexane, cycloheptane, cyclooctane, cyclononane, cyclodecane, cyclopentene, cyclohexene, cyclopentadiene, cyclohexadiene, benzene, pentalene, indene, naphthalene, azulene, fluorene, phenanthrene, anthracene, acenaphthylene, biphenylene, perhydropentalene, indane (dihydroindene), perhydroindene, dihydronaphthalene, tetrahydronaphthalene, perhydronaphthalene, perhydroazulene, perhydrofluorene, perhydrophenanthrene, perhydroanthracene, perhydroacenaphthylene, perhydrophenylene, bicyclopentane, bicyclohexane, bicycloheptane ([2.2.1]bicyclohepatane), bicyclooctane, bicyclononane, bicyclodecane, adamantane etc. Heterocyclic ring means, for example, 4-18 membered mono-, bi-, or tri-aromatic heterocyclic ring which may be partially or fully saturated containing 1 to 4 nitrogen atom(s), 1 to 2 oxygen atom(s) and/or a sulfur atom. 4-18 membered mono-, bi-, or tri-aromatic heterocyclic ring which may be partially or fully saturated containing 1 to 4 nitrogen atom(s), 1 to 2 oxygen atom(s) and/or a sulfur atom means, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, indazole, quinoline, isoquinoline, quinolizine, purine, phthalazine, pteridine, naphthyridine, quinoxaline, quinazoline, cinnoline, pyrrolopyridine, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, phenanthridine, phenanthroline, perimidine, pyridonaphthyridine, pyrazoloisoquinoline, pyrazolonaphthyridine, pyrimidoindole, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxetane, dihydrofuran, tetrahydrofuran, dihydropyran, tetrahydropyran, dihydrooxepine, tetrahydrooxepine, perhydrooxepine, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline (dihydroindole), isoindoline (dihydroisoindole (e.g. 1,3-dihydro-2H-isoindole etc.)), dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline (e.g. 3,4-dihydro-1H-isoquinoline etc.), perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, tetrahydropyrrolopyridine, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, tetrapyridonaphthyridine, tetrahydro-beta-carboline, dihydroazepinoindole, hexahydroazepinoindole, tetrahydropyrazoloisoquinoline, tetrahydropyrazolonaphthylidine, dihydroazepinoindazole, hexahydroazepinoindazole, dihydropyrazolopyridoazepine, hexahydropyrazolopyridoazepine, tetrahydropyrimidoindole, dihydrothiazinoindole, tetrahydrothiazinoindole, dihydrooxazinoindole, tetrahydrooxazinoindole, dioxolane, dioxane, benzodioxol (e.g. 1,3-benzodioxol etc.), benzodioxane, chromen, chroman and so on.

"Substituent" in "cyclic group which may have a substituent(s)" represented by ringA, for example, C1-8 alkyl (straight-chain and branched-chain alkyl e.g. methyl, ethyl, n-propyl, isopropyl, n-butyl, isobutyl, sec-butyl, tert-butyl, pentyl, hexyl, heptyl, octyl etc.), halogen atom (fluorine, chlorine, bromine, iodine), C1-4 alkoxy (straight-chain and branched-chain alkoxy, e.g. methoxy, ethoxy, n-propoxy, isopropoxy, n-butoxy, isobutoxy, sec-butoxy, tert-butoxy etc.), nitro, trihalomethyl (e.g. methyl tri-substituted with iodine atom(s), bromine atom(s), fluorine atom(s) or chlorine atom(s) etc.), trihalomethoxy (e.g. methoxy tri-substituted with iodine atom(s), bromine atom(s), fluorine atom(s) or chlorine atom(s) etc.), trihalomethylthio (e.g. methylthio tri-substituted with iodine atom(s), bromine atom(s), fluorine atom(s) or chlorine atom(s) etc.), cyano, C1-4 alkylthio (e.g. methylthio, ethylthio, n-propylthio, isopropylthio, n-butylthio, isobutylthio, sec-butylthio, tert-butylthio etc.), $NR^9R^{10}$ (wherein $R^9$ and $R^{10}$ are each independently hydrogen atom or C1-4 alkyl (straight-chain and branched-chain alkyl e.g. methyl, ethyl, n-propyl, isopropyl, n-butyl, isobutyl, sec-butyl, tert-butyl etc.)), carbocyclic ring which may have a substituent(s), heterocyclic ring which may have a substituent(s) and so on. These optional substituents may be substituted at 1-5 replaceable positions. Carbocyclic ring and heterocyclic ring in "carbocyclic ring which may have a substituent(s)" and "heterocyclic ring which may have a substituent(s)" as substituent have the same meanings as carbocyclic ring and heterocyclic ring in cyclic group represented by ringA. Substituent in "carbocyclic ring which may have a substituent(s)" and "heterocyclic ring which may have a substituent(s)" as substituent means, for example, C1-8 alkyl (straight-chain and branched-chain alkyl e.g. methyl, ethyl, n-propyl, isopropyl, n-butyl, isobutyl, sec-butyl, tert-butyl, pentyl, hexyl, heptyl, octyl etc.), halogen atom (fluorine, chlorine, bromine, iodine), C1-4 alkoxy (straight-chain and branched-chain alkoxy, e.g. methoxy, ethoxy, n-propoxy, isopropoxy, n-butoxy, isobutoxy, sec-butoxy, tert-butoxy etc.), nitro, trihalomethyl (e.g. methyl tri-substituted with iodine atom(s), bromine atom(s), fluorine atom(s) or chlorine atom(s) etc.), trihalomethoxy (e.g. methoxy tri-substituted with iodine atom(s), bromine atom(s), fluorine atom(s) or chlorine atom(s) etc.), trihalomethylthio (e.g. methylthio tri-substituted with iodine atom(s), bromine atom(s), fluorine atom(s) or chlorine atom(s) etc.), cyano, C1-4 alkylthio (e.g. methylthio, ethylthio, n-propylthio, isopropylthio, n-butylthio, isobutylthio, sec-butylthio, tert-butylthio etc.), $NR^{11}R^{12}$ (wherein $R^{11}$ and $R^{12}$ are each independently hydrogen atom or C1-4 alkyl (straight-chain and branched-chain alkyl e.g. methyl, ethyl, n-propyl, isopropyl, n-butyl, isobutyl, sec-butyl, tert-butyl etc.)) and so on. These optional substituents may be substituted at 1-5 replaceable positions.

Substituent in "a nitrogen atom which may have a substituent(s)" represented by X means, for example, C1-8 alkyl (straight-chain and branched-chain alkyl e.g. methyl, ethyl, n-propyl, isopropyl, n-butyl, isobutyl, sec-butyl, tert-butyl, pentyl, hexyl, heptyl, octyl etc.), arylalkyl (e.g. benzyl, phenetyl), phenyl, alkoxycarbonyl (tert-butoxycarbonyl) and so on.

Unless otherwise specified, all isomers are included in the present invention. For example, alkyl, alkenyl, alkynyl, alkoxy, alkylthio, alkylene alkenylene and alkynylene group means straight-chain or branched-chain ones. In addition, isomers on double bond, ring, fused ring (E-, Z-, cis-, trans-isomer), isomers generated from asymmetric carbon atom(s) (R-, S-isomer, α-, β-configuration, enantiomer, diastereomer), optically active isomers (D-, L-, d-, l-isomer), polar compounds generated by chromatographic separation (more polar compound, less polar compound), equilibrium compounds, rotational isomers, mixtures thereof at voluntary ratios and racemic mixtures are also included in the present invention.

The salts of the compounds represented by formula (I) include all of pharmaceutically acceptable ones. As pharmaceutically salts, non-toxic, water-soluble salts are preferred. The suitable salts include for example, salts of alkali metals (e.g., potassium, sodium, lithium, etc.), salts of alkaline earth metals (e.g., calcium, magnesium, etc.), ammonium salts (e.g., tetramethylammonium salt, tetrabutylammonium salt, etc.), pharmaceutical acceptable salts of organic amine (e.g., triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), acid addition salts (salts of inorganic acids (e.g., hydrochloride, hydrobromide, hydroiodide, sulfate, phosphate, nitrate etc.), and salts of organic acids (e.g., acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate etc.).

N-oxide of the compound represented by formula (I) means nitrogen atom of the compound represented by formula (I) is oxidized. The N-oxide may additionally be the above-mentioned salts of alkali (earth) metals, ammonium salts, salts of organic amine and acid addition salts.

The suitable solvates of the compound represented by formula (I) include for example, hydrates, solvates of the alcohols (e.g., ethanol etc.), and so on. The solvates are preferred to be non-toxic and water-soluble. In addition, the solvate of the compound of the present invention include solvents of salts of alkali (earth) metals, ammonium salts, salts of organic amine, acid addition salts and N-oxide etc. of the compound of the invention.

The compound of the present invention is converted into the above-mentioned salt, the above-mentioned N-oxide, the above-mentioned solvate by known methods.

The prodrug of the compounds represented by formula (I) means a compound is the compound represented by formula (I) by reaction with enzymes, gastric acids and so on within an organism. The prodrug of the compounds represented by formula (I) include, when the compounds represented by formula (I) have amino, the prodrug is the compounds the amino of which is acylated, alkylated, phosphorylated (e.g., the compounds are that the amino of the compounds represented by formula (I) is eicosanoated, alanylated, pentylaminocarbonylated, (5-methyl-2-oxo-1,3-dioxolan-4-yl)methoxycarbonylated, tetrahydrofuranated, pyrrolidylmethylated, pivaloyloxymethylated, acetoxymethylated, tert-butylated, etc.); when the compounds represented by formula (I) have hydroxyl, the prodrug is the compounds the hydroxyl of which are acylated, alkylated, phosphorylated, borated (e.g., the compounds are that the hydroxyl of the compounds represented by formula (I) are acetylated, palmitoylated, propanoylated, pivaloylated, succinylated, fumarylated, alanylated, dimethylaminomethylcarbonylated etc.); when the compounds represented by formula (I) have carboxyl, the prodrug is the compound the carboxyl of which are esterified, amidated (e.g., the compounds are that the carboxyl of the compounds represented by formula (I) is ethylesterified, isopropylesterified, phenylesterified, carboxymethylesterified, dimethylaminomethylesterified, pivaloyloxymethylesterified, ethoxycarbonyloxyethylesterified, phthalidylesterified, (5-methyl-2-oxo-1,3-dioxolen-4-yl)methylesterified, cyclohexyloxycarbonylethylesterified, methylamidated etc.); and so on. These compounds can be prepared by known method. In addition, the prodrug of the compound represented by formula (I) may be either hydrate or non-hydrate. Additionally, the prodrug of the compound represented by formula (I) may be converted into the compound represented by formula (I) under the physiological condition which is described in "the Development of Medicine" vol. 7 "Molecular Design" published in 1991 Hirokawa shoten p.p. 163-198. Further, the compound represented by formula (I) may be labeled with isotopes (e.g. $^{3}H$, $^{14}C$, $^{35}S$, $^{125}I$ etc.) and so on.

In the present invention, PPAR agonist and antagonist includes all mode of action, that is, PPAR α, γ, δ, α+γ, α+δ, γ+δ, and α+γ+δ agonist and antagonist. In addition, preferable mode of action of the present invention is PPAR δ agonist.

In the formula (I) represents the compound of the present invention, each definition represented by ringA, X, $R^1$, $R^2$ and $R^3$ is preferable. Preferable groups and preferable ring are listed below, but all the symbols used here have the same meanings as described above.

As $R^1$ or $R^2$, hydrogen atom, C1-8 alkyl, or halogen atom is preferred. Hydrogen atom, methyl, ethyl or fluorine atom is more preferred.

As $R^3$, C1-5 alkyl, C1-2 alkyl substituted with 1 to 3 halogen atom(s), or phenyl is preferred. Methyl, ethyl, propyl, isopropyl, butyl, tert-butyl, pentyl, phenyl or 2,2,2-trifluoroethyl is more preferred.

As $R^4$, hydrogen atom or C1-4 alkyl is preferred. Hydrogen atom, methyl or ethyl is more preferred.

As $R^5$ and $R^6$, hydrogen atom or C1-4 alkyl is preferred. Hydrogen atom, methyl or ethyl is more preferred. Hydrogen atom is particularly preferred.

As carbocyclic ring which $R^5$ and $R^6$ may be together with their neighboring carbon atom to form, C3-7 saturated carbocyclic ring. Cyclopropane, cyclobutane or cyclopentane is more preferred.

As X, sulfur atom or oxygen atom is preferred. Sulfur atom is more preferred.

As carbocyclic ring represented by ringA, C3-10 mono-, or bi-carbocyclic ring is preferred. Cyclopropane, cyclobutane, cyclopentane, cyclohexane, cycloheptane, cyclooctane, cyclononane, cyclodecane or benzene is more preferred. Benzene is particularly preferred.

As heterocyclic ring represented by ringA, 5-10 membered mono-, or bi-aromatic heterocyclic ring which may be partially or fully saturated containing 1 to 2 nitrogen atom(s), 1 to 2 oxygen atom(s) and/or a sulfur atom is preferred. Piperidine, piperazine, 1,3-benzodioxol, 1,3-dihydro-2H-isoindole, 3,4-dihydro-1H-isoquinoline, or 3,6-dihydro-2H-pyridine is more preferred. Piperidine or piperazine is particularly preferred.

As substituent in "cyclic group which may have a substituent(s)" represented by ringA, halogen atom, trihalomethyl, trihalomethoxy, trihalomethylthio, phenyl which may have a substituent(s) (wherein as substituent, halogen atom, C1-4 alkyl, C1-4 alkoxy), pyridyl which may have a substituent(s), thienyl, or furyl is preferred. Fluorine atom, trifluoromethyl, trifluoromethoxy, trifluoromethylthio, phenyl, pyridin-2-yl, 4-chlorophenyl, 4-fluorophenyl, 3-fluorophenyl, thiophen-2-yl, thiophen-3-yl, furan-2-yl, 4-methylphenyl, 4-methoxyphenyl, or 5-trifluoromethylpyridin-2-yl is preferred.

Processes for the Preparation of the Compound of the Present Invention:

The compound of the present invention represented by formula (I) can be prepared by combining the known processes, for example, the following processes, or the processes shown in Examples, which is the properly improved processes described in "*Comprehensive Organic Transformations: A Guide to Functional Group Preparations,* 2nd Edition "Richard C. Larock, Wiley & Sons Inc, 1999" and so on. Still, ingredients may be used as salts in the following each processes for the preparation. As these salts, the salts described as salts of the above-mentioned formula (I) are used.

The compound represented by formula (I) can be prepared by Mitsunobu reacting a compound represented by formula (II)

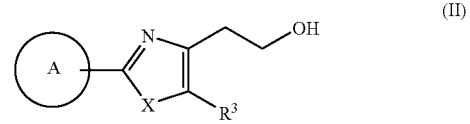

wherein all symbols have the same meanings as those defined above, with a compound represented by formula (III)

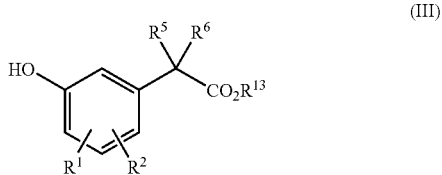

(III)

wherein $R^{13}$ is C1-8 alkyl, or protection group of carboxyl, the other symbols have the same meanings as those defined above,
and the compound represented by formula (I-1)

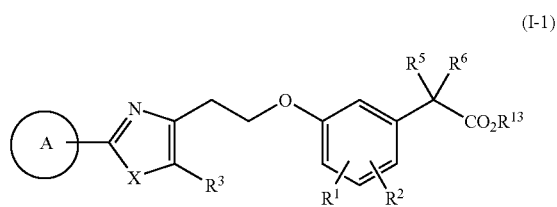

(I-1)

wherein all symbols have the same meanings as those defined above,
is obtained, if necessary, followed by subjecting to a deprotection reaction of the protective group of carboxyl.

This Mitsunobu reaction is known. It is carried out, for example, by reacting with the corresponding alcohol compound in an organic solvent (e.g., dichloromethane, diethylether, tetrahydrofuran, acetonitrile, benzene, toluene, etc.) in the presence of azo compound (e.g. diethyl azodicarboxylate (DEAD), diisopropyl azodicarboxylate, 1,1'-(azodicarbonyl) dipiperidine (ADDP), 1,1'-azobis(N,N-dimethylformamide) etc.) and phosphine compound (e.g. triphenylphosphine, tributylphosphine, trimethylphosphine, polymer support triphenylphosphine etc.) at a temperature of 0 to 60° C.

The protection group for carboxyl includes, for example, methyl, ethyl, allyl, t-butyl, trichloroethyl, benzyl (Bn), phenacyl, p-methoxybenzyl, trityl, 2-chlorotrityl or solid phase carrier binding a group thereof and so on. The protective group for carboxyl is not particularly limited to the above mentioned groups, so long as it can be easily and selectively left. For example, those described in *Protective Groups in Organic Synthesis*, (T. W. Greene, John Wiley & Sons Inc, 1999) can be used.

The deprotection reaction of carboxyl is known, and it includes
(1) alkaline hydrolysis,
(2) deprotection reaction under acidic conditions,
(3) deprotection reaction by hydrogenolysis,
(4) deprotection reaction of a silyl group,
(5) deprotection reaction using metals,
(6) deprotection reaction using metal complexes, and so on.
These methods are described concretely as follows.

(1) The deprotection reaction by alkaline hydrolysis is, for example, carried out in an organic solvent (e.g., methanol, tetrahydrofuran, or dioxane etc.) using a hydroxide of an alkali metal (e.g., sodium hydroxide, potassium hydroxide, or lithium hydroxide etc.), a hydroxide alkaline earth metal (e.g., barium hydroxide, or calcium hydroxide etc.), or a carbonate (e.g., sodium carbonate or potassium carbonate, etc.), or an aqueous solution thereof, or a mixture thereof at a temperature of 0 to 40° C.

(2) The deprotection reaction under acidic conditions is carried out, for example, in an organic solvent (e.g., dichloromethane, chloroform, dioxane, ethyl acetate, or anisole etc.) in an organic acid (e.g., acetic acid, trifuloroacetic acid, methansulfonic acid, or p-tosylate, etc.), or an inorganic acid (e.g., hydrochloric acid, or sulfuric acid, etc.) or a mixture thereof (e.g., hydrogen bormide/acetic acid, etc.) at a temperature of 0 to 100° C.

(3) The deprotection reaction by hydrogenolysis is carried out, for example, in a solvent (e.g., ethers (e.g., tetrahydrofuran, dioxane, dimethoxyethane (DME), or diethylether, etc.), alcohols (e.g., methanol, or ethanol, etc.), benzenes (e.g., benzene, or toluene etc.), ketones (e.g. acetone, or methylethylketone, etc.), nitriles (e.g., actetonitrile etc.), amides (e.g., DMF etc.), water, ethyl acetate, acetic acid, or a mixed solvent of at least two of these etc.) in the presence of a catalyst (e.g., palladium-carbon, palladium black, palladium hydroxide-carbon, platinum oxide, or Raney nickel, etc.) under the hydrogen atmosphere at normal pressure or under pressurization, or in the presence of ammonium formate at a temperature of 0 to 200° C.

(4) The deprotection reaction of a silyl group is carried out, for example, in a water-miscible organic solvent (e.g., tetrahydrofuran, or acetonitrile, etc.) using tetrabutylammonium fluoride at a temperature of 0 to 40° C.

(5), The deprotection reaction using metals is carried out, for example, in an acidic solvent (e.g., acetic acid, pH4.2-7.2 buffer solution, or a mixture of a solution thereof and an organic solvent of tetrahydrofran etc.) in the presence of zinc powder, if necessary sonicating, at the temperature of 0 to 40° C.

(6) The deprotection reaction using metal complexes is carried out, for example, in an organic solvent (e.g., dichloromethane, DMF, THF, ethyl acetate, acetonitrile, dioxane, ethanol etc.), water, or a mixture thereof, in the presence of a trap reagent (e.g., tributyltine hydride, triethylsilane, dimedone, morpholine, diethylamine, pyrrolidine, etc.), an organic acid (e.g., acetic acid, formic acid, 2-ethyl hexanoic acid, etc.) and/or salts of organic acid (e.g., sodium 2-ethylhexanoate, potassium 2-ethylhexanoate etc.), in the presence or absence of a phosphine reagent (e.g., triphenylphosphine etc.), using metal complexes (e.g., tetrakistriphenylphosphinepalladium(0), dichlorobis(triphenylphosphine)palladium(II), palladium acetate(II), tris(triphenylphosphine) rhodium(I) chloride etc.) at the temperature of 0 to 40° C.

In addition, the deprotection reaction except the above-mentioned processes can be carried out, for example, by the process described in T. W. Greene, *Protective Groups in Organic Synthesis*, Wiley, New York, 1999. As is easily understood by those skilled in the art, the intended compounds of the invention may be readily prepared through selective use of these deprotection reactions.

The compound represented by formula (II) or (III) as starting materials or reagents are known in themselves, or can be easily prepared by the method described in Example below or known method, for example, the method described in "*Comprehensive Organic Transformations: A Guide to Functional Group Preparations,* 2nd Edition (Richard C. Larock, John Wiley & Sons Inc, 1999)".

In each reaction in the present specification, as will be understood by those skilled in the art, the reaction with heating can be performed using water bath, oil bath, sand bath or microwave.

In each reaction in the present specification, solid-phase supported reagent accordingly supported to macromolecule polymer (e.g. polystyrene, polyacrylamide, polypropylene, polyethyleneglycol etc.) may be used.

In each reaction in the present specification, reaction products may be purified in an ordinary manner, for example, through normal-pressure or reduced-pressure distillation, or through high-performance liquid chromatography with silica gel or magnesium silicate, thin-layer chromatography, or column chromatography, ion-exchange resin, scavenger resin or through washing or recrystallization and so on. The purification may be effected in each reaction stage or after some reaction stages.

Pharmacological Activity:

As pharmacological test other than ones described in Example, particularly in vivo measurement using animals, for example, there are methods as follows. The hypoglycemic effect and hypolipidemic effect of the compound of the invention can be measured by methods as follows.

Hypoglycemic and Hypolipidemic Effects (1):

The body weight and blood glucose level of KKAy/Ta Jcl mice are measured and mice are divided into some groups based on blood glucose level. For six days after the next day, mice are bred by being given pellets including the compound of the present invention or milled pellets. After repeated administration, the body weight and the food intake of mice are measured and average food intakes are converted into the administration dose. In addition, blood glucose level, plasma triglyceride (TG) level, plasma insulin, non-esterified fatty acid (NEFA), GOT and GPT levels are measured.

It is suggested the possibility as an agent for preventing and/or treating of diabetes mellitus, hyperlipidemia, atherosclerosis etc., from lowering effects of plasma glucose, plasma insulin, NEFA or plasma TG levels in well-fed KKAy/Ta mice.

Hypoglycemic and Hypolipidemic Effects (2):

The body weight, blood glucose level, NEFA, TG and HbA1c level of Zucker fa/fa rat (Strain: Crj-[ZUC]-fa/fa) and normal control animal, lean rat (Strain: Crj-[ZUC]-lean) are measured. These rats are divided into some groups based on HbA1c level and body weight among these. After the next day, the compounds of the present invention are orally repeatedly administered. In addition, vehicles are administered into control.

After repeated administration onset, average food intakes are calculated and blood glucose, NEFA, TG and HbA1c level are measured. In addition, oral glucose tolerance test (OGTT) is performed to evaluate improving effect on glucose intolerance. Rats are fasted on the previous day to perform OGTT. The next day, rats are loaded at a volume of 2 g/5 ml/kg of glucose solution, and then 60 and 120 minutes after loading, plasma insulin, NEFA, TG, GOT, GPT and liver wet weight are measured.

It is suggested the possibility as an agent for preventing and/or treating of diabetes mellitus, hyperlipidemia, atherosclerosis etc., from lowering effects of plasma glucose, plasma insulin, NEFA, HbA1c levels or plasma TG level in well-fed Zucker fa/fa rats. Also, a decrease effect of fasting plasma glucose and improving effect of glucose intolerance during OGTT suggest the possibility as an agent for preventing and/or treating of diabetes mellitus.

Hypocholesterolemic and Hypolipidemic Effects (3):

High cholesterol diets (CRF-1 solid pellet mixed of 5.5% peanut oil, 1.5% cholesterol, 0.5% cholic acid, Oriental Bio Service) are loaded to SD rats and then the body weight of food-deprived rats are measured, various parameter levels below are measured. The measurement items are LDL, HDL, TG level, NEFA, and TC level. Rats are divided into some groups based on HDL level. From the next day to six days in a row, the suspended solution of the compounds in vehicle (0.5% methylcellulose aqueous solution) are orally compellingly administered once daily and the loading of high cholesterol diets is continued. After termination of final administration, plasma lipid (TG, HDL, LDL, NEFA, TC level) is measured.

It is suggested the possibility as an agent for preventive and/or therapeutic agent for hyperlipidemia, atherosclerosis etc., from lowering effects of plasma TG level, TC level, and LDL level in fasted SD rats.

Hypoglycemic and Hypolipidemic Effects (4):

Cynomolgus monkeys are performed a medical inspection and habituated at test operation facilities. The body weight of animals is measured, the animals are divided into some groups and vehicle or the drug solution including 3 to 100 mg/kg/day compounds of the present invention are repeatedly intranasally intragastric administered once a day using nutrition catheters and injection syringes. After the administration, blood samples are collected and the above-mentioned hematological test (measurement of the number of red blood cells, hematocrit, hemoglobin content, the number of platelets and the number of leukocytes) and blood biochemical test (measurement of GOT, GPT, alkaline phosphatase, total protein, blood urea nitrogen, creatinine, creatinine kinase, total bilirubin, blood glucose, total cholesterol, HDL, LDL and TG) are performed. In addition, before the administration onset of the compounds of the present invention and 14th days after administration onset, blood sample were collected at 1, 2 and 4 hours after administration, and at 1, 2 and 3 hours after feeding a diet (intake time for an hour), to measure blood glucose, total cholesterol, HDL, LDL and TG.

It is suggested that the lowering effect of plasma TG levels, TC levels and LDL levels in fasted normal cynomolgus monkeys has possibility as the preventing and/or therapeutic agent for hyperlipidemia and atherosclerosis and so on. It is also observed in inhibitory effect on TG rising postprandial. In addition, it is suggested that inhibitory effect of blood glucose after dietary loading has possibility as the preventing and/or therapeutic agent for diabetes. Additionally, it can be estimated whether compounds have a toxicity change or not from other blood biochemical parameters.

Toxicity:

Toxicity of the compound represented by formula (I) is very low, and it is safe enough to use as a pharmaceutical agent.

Application to Pharmaceutical Preparations:

Since the compound represented by formula (I) of the present invention, a salt thereof, a solvent thereof or a prodrug thereof have a PPAR δ agonistic activity, for example, HDL cholesterol elevating effect, LDL clearance increasing effect, lipid, especially cholesterol carrying promoting effect and reverse transmission promoting effect, macrophage foam cell formation suppressive effect, cholesterol biosynthesis inhibitory effect, it is expected to be applied as agents for preventing and/or treating of diseases associated with glucose/lipid metabolic disorders (such as diabetes, hyperlipidemia (hypercholesterolemia, hypo-HDL-cholesterolemia, hyper-LDLcholesterolemia, hypertriglyceridemia etc.), atherosclerosis, cardiovascular disease, obesity, metabolic syndrome etc.), hypertension, circulatory diseases, dermal inflammatory disorder etc.

The compound represented by formula (I) or a salt thereof, a solvent thereof or a prodrug thereof may be administered in combination with other drugs for the purpose of
1) complement and/or enhancement of preventing and/or treating effect,
2) improvement of dynamics and absorption of the compound, and lowering of dose, and/or
3) alleviation of side effect of the compound.

The compound represented by formula (I), a salt thereof, a solvent thereof or a prodrug thereof and other pharmaceutical preparations may be administered in the form of formulation having these components incorporated in one preparation or may be administered in separate preparations. In the case where these pharmaceutical preparations are administered in separate preparations, they may be administered simultaneously or at different times. In the latter case, the compound represented by formula (I), a salt thereof, a solvent thereof or a prodrug thereof may be administered before the other pharmaceutical preparations. Alternatively, the other pharmaceutical preparations may be administered before the compound represented by formula (I), a salt thereof, a solvent thereof or a prodrug thereof. The method for the administration of these pharmaceutical preparations may be the same or different.

The other pharmaceutical preparations may be low-molecular compounds. In addition, they may be macromolecular protein, polypeptide, polynucleotide (DNA, RNA, and gene), antisense, decoy, antibody or vaccine and so on. The dose of the other pharmaceutical preparations can be accordingly selected as a standard of clinical dose. Additionally, the compounding ratio of the compounds in the present invention and the other pharmaceutical preparations can be accordingly selected by the age and body weight of administering object, the administration method, the administration time, the object disease, the symptom, the combination etc. For example, the other pharmaceutical preparations may be used from 0.01 to 100 parts by weight relative to 1 part by weight of the compounds in the present invention. The other pharmaceutical preparations may be administered at appropriate ratio combining one or more arbitrarily agents.

The diseases on which the preventive and/or treatment effect of the above-mentioned combined preparations works are not specifically limited but may be those for which the preventive and/or treatment effect of the compound represented by formula (I), a salt thereof, a solvent thereof or a prodrug thereof is compensated for and/or enhanced.

As other drugs to compensate and/or enhance for hypolipidemic effect of the compound represented by formula (I), a salt thereof, a solvent thereof or a prodrug thereof, i.e. lipid improvement agents, they include, for example, MTP (Microsomal Triglyceride Transfer Protein) inhibitor, HMG-CoA reductase inhibitor, squalene synthase inhibitor, fibrate (fibric acid derivative), ACAT (acyl CoA: Cholesterol O-acyl-transferase) inhibitor, 5-lipoxygenase inhibitor, cholesterol absorption inhibitor, bile acid absorption inhibitor, ileal $Na^+$/bile acid transporter (IBAT) inhibitor, LDL receptor activator/expression enhancer, pancreatic lipase inhibitor, probucol formulation, nicotine acid formulation, cholesteryl-ester transfer protein (CETP) inhibitor, other anti-hypercholesterolemia therapeutic agent and so on.

Examples of MTP inhibitor include BMS-201038, BMS-212122, BMS-200150, GW-328713, R-103757 and so on. Examples of HMG-CoA reductase inhibitor include atorvastatin, fulvastatin, lovastatin, pitavastatin, pravastatin, rosuvastatin, simvastatin, and so on. Examples of ACAT inhibitor include F-12511, F-1394, CI-1011, melinamide and so on. Examples of squalene synthase inhibitor include TAK-475 and so on. Examples of fibrate include gemfibrozil, clofibrate, bezafibrate, fenofibrate, clinofibrate, simfibrate and so on. Examples of ACAT inhibitor include CI-1101, FCE27677, RP73163 and so on. Examples of cholesterol absorption inhibitor include ezetimibe, soysterol and so on. Examples of bile acid absorption inhibitor include cholestyramine, colesevelam, colestimide and so on. Examples of LDL receptor activator/expression enhancer include MD-700, LY295427 and so on. Examples of pancreatic lipase inhibitor include orlistat and so on. It is known that there are sometimes associated with rhabdomyolysis in case of a combination of fibrate and HMG-CoA reductase inhibitor and this combination are contraindicated in renal failure patients and patients with impaired renal function. In the combination of the compounds of the present invention, a salt thereof, a solvate thereof, or a prodrug thereof and the above-mentioned lipid improvement drugs, there is possibility to correct abnormal lipid metabolism without developing rhabdomyolysis. As combination drugs which are combination with the compounds of the present invention, a salt thereof, a solvate thereof, or a prodrug thereof, HMG-CoA reductase inhibitor, fibrate (fibric acid derivative), cholesterol absorption inhibitor, bile acid absorption inhibitor, pancreatic lipase inhibitor, nicotine acid formulation is preferred.

As other drugs to compensate and/or enhance for hypoglycemic effect of the compound represented by formula (I), a salt thereof, a solvate thereof, or a prodrug thereof and to enhance effect of the treatment of complication of diabetes, i.e. therapeutic agents for diabetes, they include, for example, sulfonylurea type hypoglycemic agent, biguanide preparation, alfa-glucosidase inhibitor, fast-acting insulin secretion accelerator, insulin preparation, dipeptidyl peptidase (DPP) 4 inhibitor, GLP-1 agonist, beta-3 adrenaline receptor activator, therapeutic agents for complication of diabetes and so on.

Examples of sulfonylurea type hypoglycemic agents include acetohexamide, glibenclamide, gliclazide, glyclopyramide, chlorpropamide, tolazamide, tolbutamide and glimepiride and so on. Examples of biguanide preparations include buformin hydrochloride and metformin hydrochloride and so on. Examples of alfa-glucosidase inhibitors include acarbose and voglibose and so on. Examples of fast-acting insulin secretion accelerators include nateglinide and repaglinide and so on. Examples of DPP4 inhibitor include NVP-DPP728A and so on. Examples of GLP-1 agonists include exendin 4 and so on. Examples of beta-3 adrenaline receptor activators include AJ-9677, BMS-210285, CP-331679, KUL-1248, LY-362884, L-750335 CP331648 and so on. Examples of therapeutic agents for complication of diabetes include epalrestat, zenarestat, fidarestat, zopolrestat, AS-3201, SG-210 and so on.

As other drugs to compensate and/or enhance for anti-adiposity effect of the compound represented by formula (I), a salt thereof, a solvate thereof, or a prodrug thereof, i.e. anti-adiposity agents, they include, for example, appetite suppressing agent, pancreatic lipase inhibitor, beta-3 adrenaline receptor activator, serotonin norepinephrine dopamine reuptake inhibitor and so on. Examples of appetite suppressing agent include leptin, mazindol, amphetamine, methamphetamine and so on. Examples of pancreatic lipase inhibitor include orlistat and so on. Examples of beta-3 adrenaline receptor activator include AJ-9677, BMS-210285, CP-331679, KUL-1248, LY-362884, L-750335, CP-331648, and so on. Examples of serotonin norepinephrine dopamine reuptake inhibitor include sibutramine and so on.

The weight proportion of the compound represented by formula (I), a salt thereof, a solvate thereof, or a prodrug thereof and the other drugs is not specifically limited.

Arbitrary two or more of the other drugs may be administered in combination.

Examples of the other pharmaceutical preparations for compensating for and/or enhancing the preventive and/or treatment effect of the compound represented by formula (I), a salt thereof, a solvate thereof, or a prodrug thereof include not only those which have so far been found but also those which will be found on the basis of the above-mentioned mechanism.

In order to use the compound of the invention represented by formula (I), a salt thereof, a solvate thereof, or a prodrug thereof, or the compound represented by formula (I), a salt thereof, a solvate thereof, or a prodrug thereof in combination with the other pharmaceutical preparations, these compounds are normally administered to the entire of human body or topically orally or parenterally.

The dose of these compounds depends on the age, weight and symptom of the patient, the remedial value, the administration method, the treatment time, etc. In practice, however, these compounds are administered orally once or several times per day each in an amount of from 1 mg to 1000 mg per adult, parenterally once or several times per day each in an amount of from 1 mg to 100 mg per adult or continuously administered into vein for 1 hour to 24 hours per day.

It goes without saying that the dose of these compounds may be less than the above-mentioned value or may need to exceed the above-mentioned range because the dose varies under various conditions as mentioned above.

When the compounds of the invention represented by formula (I), a salt thereof, a solvate thereof, or a prodrug thereof, or the compound represented by formula (I), a salt thereof, a solvate thereof, or a prodrug thereof is administered in combination with the other pharmaceutical preparations, they are used in the form of solid or liquid agent for oral administration, injection, agent for external application, suppository, eye drops or inhalant for parenteral administration or the like.

Examples of the solid agent for oral administration include tablet, pill, capsule, powder, and pellet. Examples of the capsule include hard capsule, and soft capsule.

In such a solid agent for internal application, one or more active materials are used in the form of preparation produced by an ordinary method singly or in admixture with a vehicle (e.g., lactose, mannitol, glucose, microcrystalline cellulose, starch etc.), binder (e.g., hydroxypropyl cellulose, polyvinyl pyrrolidone, magnesium metasilicoaluminate etc.), disintegrant (e.g., calcium fibrinoglycolate etc.), glidant (e.g., magnesium stearate etc.), stabilizer, dissolution aid (e.g., glutamic acid, aspartic acid etc.) or the like. The solid agent may be coated with a coating agent (e.g., white sugar, gelatin, hydroxypropyl cellulose, hydroxypropyl methyl cellulose phthalate etc.) or two or more layers. Alternatively, the solid agent may be capsulized by an absorbable material such as gelatin.

Examples of the liquid agent for oral administration include pharmaceutically acceptable aqueous solution, suspension, emulsion, syrup, and elixir. In such a liquid agent, one or more active agents are dissolved, suspended or emulsified in a commonly used diluent (e.g., purified water, ethanol, mixture thereof etc.). Furthermore, such a liquid agent may comprise a wetting agent, a suspending agent, an emulsifier, a sweetening agent, a flavor, a preservative, a buffer, etc.

The agent for parenteral administration may be in the form of, e.g., ointment, gel, cream, wet compress, paste, liniment, nebula, inhalant, spray, aerosol, eye drops, collunarium or the like. These agents each contain one or more active materials and are prepared by any known method or commonly used formulation.

The ointment is prepared by any known or commonly used formulation. For example, one or more active materials are triturated or dissolved in a base to prepare such an ointment. The ointment base is selected from known or commonly used materials. In some detail, higher aliphatic acid or higher aliphatic acid ester (e.g., adipic acid, myristic acid, palmitic acid, stearic acid, oleic acid, adipic acid ester, myristic acid ester, palmitic acid ester, stearic acid ester, oleic acid ester etc.), wax (e.g., beeswax, whale wax, ceresin etc.), surface active agent (e.g., polyoxyethylenealkylether phosphoric acid ester etc.), higher alcohol (e.g., cetanol, stearyl alcohol, setostearyl alcohol etc.), silicon oil (e.g., dimethyl polysiloxane etc.), hydrocarbon (e.g., hydrophilic petrolatum, white petrolatum, purified lanolin, liquid paraffin etc.), glycol (e.g., ethylene glycol, diethylene glycol, propylene glycol, polyethylene glycol, macrogol etc.), vegetable oil (e.g., castor oil, olive oil, sesame oil, turpentine oil), animal oil (mink oil, vitelline oil, squalane, squalene), water, absorption accelerator and rash preventive may be used singly or in admixture of two or more thereof. The base may further comprise a humectant, a preservative, a stabilizer, an antioxidant, a perfume, etc.

The gel is prepared by any known or commonly used formulation. For example, one or more active materials are dissolved in a base to prepare such a gel. The gel base is selected from known or commonly used materials. For example, lower alcohol (e.g., ethanol, isopropyl alcohol etc.), gelling agent (e.g., carboxymethyl cellulose, hydroxyethyl cellulose, hydroxypropyl cellulose, ethyl cellulose etc.), neutralizing agent (e.g., triethanolamine, diisopropanolamine etc.), surface active agent (e.g., polyethylene glycol monostearate etc.), gums, water, absorption accelerator, and rash preventive are used singly or in admixture of two or more thereof. The gel base may further comprise a preservative, an antioxidant, a perfume, etc.

The cream is prepared by any known or commonly used formulation. For example, one or more active materials are dissolved in a base to prepare such a cream. The cream base is selected from known or commonly used materials. For example, higher aliphatic acid ester, lower alcohol, hydrocarbon, polyvalent alcohol (e.g., propylene glycol, 1,3-butylene glycol etc.), higher alcohol (e.g., 2-hexyl decanol, cetanol etc.), emulsifier (e.g., polyoxyethylene alkyl ethers, aliphatic acid esters etc.), water, absorption accelerator, and rash preventive are used singly or in admixture of two or more thereof. The cream base may further comprise a preservative, an antioxidant, a perfume, etc.

The wet compress is prepared by any known or commonly used formulation. For example, one or more active materials are dissolved in a base to prepare a kneaded mixture which is then spread over a support to prepare such a wet compress. The wet compress base is selected from known or commonly used materials. For example, thickening agent (e.g., polyacrylic acid, polyvinyl pyrrolidone, gum arabic, starch, gelatin, methyl cellulose etc.), wetting agent (e.g., urea, glycerin, propylene glycol etc.), filler (e.g., kaolin, zinc oxide, talc, calcium, magnesium etc.), water, dissolution aid, tackifier, and rash preventive may be used singly or in admixture of two or more thereof. The wet compress base may further comprise a preservative, an antioxidant, a perfume, etc.

The pasting agent is prepared by any known or commonly used formulation. For example, one or more active materials are dissolved in a base to prepare a kneaded mixture which is then spread over a support to prepare such a pasting agent.

The pasting agent base is selected from known or commonly used materials. For example, polymer base, fat and oil, higher aliphatic acid, tackifier and rash preventive may be used singly or in admixture of two or more thereof. The pasting agent base may further comprise a preservative, an antioxidant, a perfume, etc.

The liniment is prepared by any known or commonly used formulation. For example, one or more active materials are dissolved, suspended or emulsified in water, alcohol (e.g., ethanol, polyethylene glycol etc.), higher aliphatic acid, glycerin, soap, emulsifier, suspending agent, etc., singly or in combination of two or more thereof, to prepare such a liniment. The liniment may further comprise a preservative, an antioxidant, a perfume, etc.

The nebula, inhalant, spray and aerosol each may comprise a commonly used diluent, additionally, a stabilizer such as sodium hydrogen sulfite and a buffer capable of providing isotonicity such as isotonic agent (e.g., sodium chloride, sodium citrate, or citric acid etc.). For the process for the preparation of spray, reference can be made to U.S. Pat. Nos. 2,868,691 and 3,095,355.

The injection for parenteral administration consists of solid injection used to be dissolved or suspended in the form of solution, suspension, emulsion and a solvent to be dissolved before use. The injection is prepared by dissolving, suspending or emulsifying one or more active materials in a solvent. As such a solvent there may be used distilled water for injection, physiological saline, vegetable oil, alcohol such as propylene glycol, polyethylene glycol and ethanol, etc., singly or in combination thereof. The injection may further comprise a stabilizer, a dissolution aid (e.g., glutamic acid, aspartic acid, Polysolvate 80 (trade name) etc.), a suspending agent, an emulsifier, a soothing agent, a buffer, a preservative, etc. The injection is sterilized at the final step or prepared by an aseptic process. Alternatively, an aseptic solid agent such as freeze-dried product which has previously been prepared may be rendered aseptic or dissolved in an aseptic distilled water for injection or other solvents before use.

The inhalant for parenteral administration may be in the form of aerosol, powder for inhalation or liquid for inhalation. The liquid for inhalation may be dissolved or suspended in water or other proper medium in use.

These inhalants are prepared by a known method.

For example, the liquid for inhalation is prepared from materials properly selected from preservatives (e.g., benzalconium chloride, Paraben etc.), colorants, buffering agents (e.g., sodium phosphate, sodium acetate etc.), isotonic agents (e.g., sodium chloride, concentrated glycerin etc.), thickening agents (e.g., carboxyvinyl polymer etc.), absorption accelerators, etc. as necessary.

The powder for inhalation is prepared from materials properly selected from glidants (e.g., stearic acid and salt thereof etc.), binders (e.g., starch, dextrin etc.), vehicles (e.g., lactose, cellulose etc.), colorants, preservatives (e.g., benzalconium chloride, Paraben etc.), absorption accelerators, etc., if necessary.

In order to administer the liquid for inhalation, a sprayer (e.g., atomizer, nebulizer etc.) is normally used. In order to administer the powder for inhalation, a powder inhaler is normally used.

Other examples of the composition for parenteral administration include suppository for rectal administration and pessary for vaginal administration prepared by an ordinary formulation comprising one or more active materials.

Effect of the Invention

Since the compound represented by formula (I) of the present invention and nontoxic salt thereof have a PPAR δ agonistic activity, for example, HDL cholesterol elevating effect, LDL clearance increasing effect, lipid, especially cholesterol carrying promoting effect and reverse transmission promoting effect, and cholesterol biosynthesis inhibitory effect, it is expected to be applied as agents for preventing and/or treating of diseases associated with glucose•lipid metabolic disorders (such as diabetes, hyperlipidemia (hypercholesterolemia, hypo-HDL-cholesterolemia, hyper-LDL-cholesterolemia, hypertriglyceridemia etc.), atherosclerosis, cardiovascular disease, obesity, metabolic syndrome etc.), hypertension, circulatory diseases, dermal inflammatory disorder etc.

BEST MODE FOR CARRYING OUT THE INVENTION

The present invention is explained below in detail based on Examples, however, the present invention is not limited thereto. The solvents in parentheses at chromatographic separations section and TLC section show the developing or eluting solvents and the ratios of the solvents used are indicated by volume. NMR is the measurement of $^1$H NMR and the solvents in parentheses indicated in NMR section show solvents used in determination.

The compound names used in the specification are named by using of ACD/Name (Trade mark, Advanced Chemistry Development Inc.) or ACD/Name batch (Trade mark, Advanced Chemistry Development Inc.) which is the computer program to name according to IUPAC rule, or according to IUPAC organic chemistry nomenclature

EXAMPLE 1 methyl [3-(2-{5-ethyl-2-[4-(trifluoromethoxy)phenyl]-1,3-oxazol-4-yl}ethoxy)-4-methylphenyl]acetate:

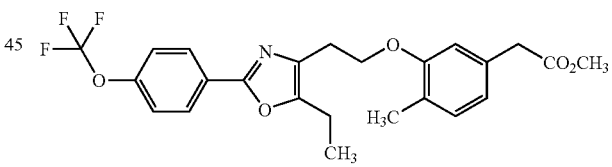

Under atmosphere of argon, a solution of methyl (3-hydroxy-4-methylphenyl)acetate (1.00 g) in methylene chloride (22 mL) was added by 2-{5-ethyl-2-[4-(trifluoromethoxy)phenyl]-1,3-oxazol-4-yl}ethanol (2.00 g), triphenylphosphine (2.18 g) and 1,1'-(azodicarbonyl)dipiperidine (2.10 g) and stirred overnight at room temperature. The reaction mixture was concentrated and the obtained residue was purified by column chromatography on silica gel (hexane:ethyl acetate=4:1) to give the title compound (2.38 g) having the following physical data.

TLC: Rf 0.62 (hexane:ethyl acetate=2:1);

$^1$H NMR (CDCl$_3$): δ 8.05-7.99 (m, 2H), 7.30-7.24 (m, 2H), 7.05 (d, J=7.5 Hz, 1H), 6.77-6.72 (m, 2H), 4.24 (t, J=6.5 Hz, 2H), 3.67 (s, 3H), 3.56 (s, 2H), 3.00 (t, J=6.5 Hz, 2H), 2.75 (q, J=7.5 Hz, 2H), 2.15 (s, 3H), 1.29 (t, J=7.5 Hz, 3H).

EXAMPLE 2

[3-(2-{5-ethyl-2-[4-(trifluoromethoxy)phenyl]-1,3-oxazol-4-yl}ethoxy)-4-methylphenyl]acetic acid

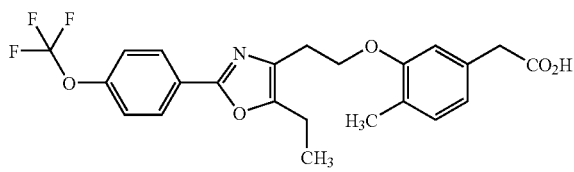

A mixed solution of the compound prepared in Example 1 (1.90 g) in tetrahydrofuran (10 mL) and methanol (10 mL) was added by 2N sodium hydroxide aqueous solution (10 mL) and stirred for thirty minutes at room temperature. The reaction mixture was added by 1N hydrochloric acid (25 mL) and extracted by ethyl acetate. The organic layer was washed with saturated brine, dried over anhydrous magnesium sulfate and then the filtrate was concentrated to give the title compound (3.66 g) having the following physical data.

TLC: Rf 0.40 (chloroform:methanol=9:1);
$^1$H NMR (CDCl$_3$): δ 8.00 (m, 2H), 7.25 (d, J=8.1 Hz, 1H), 7.05 (d, J=8.1 Hz, 1H), 6.76-6.71 (m, 3H), 4.22 (t, J=6.6 Hz, 2H), 3.58 (s, 2H), 2.99 (t, J=6.6 Hz, 2H), 2.76 (q, J=7.5 Hz, 2H), 2.14 (s, 3H), 1.29 (t, J=7.5 Hz, 3H).

EXAMPLE 3-EXAMPLE 27

By the same procedure as described in Example 1 and 2 using methyl (3-hydroxy-4-methylphenyl)acetate or the corresponding alcohol derivative instead thereof and methyl (3-hydroxy-4-methylphenyl)acetate and the corresponding alcohol derivative instead of 2-{5-ethyl-2-[4-(trifluoromethoxy)phenyl]-1,3-oxazol-4-yl}ethanol, the following compounds of the present invention were obtained.

EXAMPLE 3

[3-(2-{5-methyl-2-[4-(trifluoromethyl)piperidin-1-yl]-1,3-thiazol-4-yl}ethoxy)phenyl]acetic acid:

TLC: Rf 0.49 (chloroform:methanol=10:1);
$^1$H NMR (CDCl$_3$): δ 7.24-7.17 (m, 1H), 6.87-6.77 (m, 3H), 4.16 (t, J=7.0 Hz, 2H), 4.00 (brd, J=13.0 Hz, 2H), 3.59 (s, 2H), 2.93 (t, J=7.0 Hz, 2H), 2.90 (dt, J=2.5, 13.0 Hz, 2H), 2.29-2.12 (m, 1H), 2.24 (s, 3H), 1.93 (brd, J=13.0 Hz, 2H), 1.67 (dq, J=4.5, 13.0 Hz, 2H).

EXAMPLE 4

[3-(2-{5-propyl-2-[4-(trifluoromethyl)phenyl]-1,3-oxazol-4-yl}ethoxy)phenyl]acetic acid:

TLC: Rf 0.52 (chloroform:methanol=10:1);
$^1$H NMR (CDCl$_3$): δ 8.08 (d, J=8.0 Hz, 2H), 7.67 (d, J=8.0 Hz, 2H), 7.22 (td, J=7.5, 1.0 Hz, 1H), 6.82 (m, 3H), 4.23 (t, J=6.5 Hz, 2H), 3.60 (s, 2H), 2.99 (t, J=6.5 Hz, 2H), 2.70 (t, J=7.5 Hz, 2H), 1.74 (sext, J=7.5 Hz, 2H), 1.00 (t, J=7.5 Hz, 3H).

EXAMPLE 5

[3-(2-{5-isopropyl-2-[4-(trifluoromethyl)phenyl]-1,3-oxazol-4-yl}ethoxy)phenyl]acetic acid:

TLC: Rf 0.49 (chloroform:methanol=10:1);
$^1$H NMR (CDCl$_3$): δ 8.08 (d, J=8.0 Hz, 2H), 7.67 (d, J=8.0 Hz, 2H), 7.21 (dt, J=7.5, 1.0 Hz, 1H), 6.82 (m, 3H), 4.22 (t, J=6.6 Hz, 2H), 3.60 (s, 2H), 3.17 (sept, J=7.0 Hz, 1H), 3.00 (t, J=6.5 Hz, 2H), 1.34 (d, J=7.0 Hz, 6H).

EXAMPLE 6

[4-methyl-3-(2-{5-propyl-2-[4-(trifluoromethyl)phenyl]-1,3-oxazol-4-yl}ethoxy)phenyl]acetic acid:

TLC: Rf 0.50 (chloroform:methanol=9:1);
$^1$H NMR (DMSO-d$_6$): δ 12.22 (brs, 1H), 8.09 (d, J=8.4 Hz, 2H), 7.83 (d, J=8.4 Hz, 2H), 7.00 (d, J=7.5 Hz, 1H), 6.84 (s, 1H), 6.69 (d, J=7.5 Hz, 1H), 4.19 (t, J=6.3 Hz, 2H), 3.47 (s, 2H), 2.96 (t, J=6.3 Hz, 2H), 2.70 (t, J=7.2 Hz, 2H), 2.02 (s, 3H), 1.66-1.59 (m, 2H), 0.91 (t, J=7.2 Hz, 3H).

EXAMPLE 7

[3-(2-{5-isopropyl-2-[4-(trifluoromethyl)phenyl]-1,3-oxazol-4-yl}ethoxy)-4-methylphenyl]acetic acid:

TLC: Rf 0.47 (chloroform:methanol=9:1);
$^1$H NMR (DMSO-d$_6$): δ 12.22 (brs, 1H), 8.10 (d, J=8.4 Hz, 2H), 7.84 (d, J=8.4 Hz, 2H), 7.00 (d, J=7.2 Hz, 1H), 6.84 (d, J=1.2 Hz, 1H), 6.68 (dd, J=7.2 Hz, 1.2 Hz, 1H), 4.20 (t, J=6.3 Hz, 2H), 3.46 (s, 2H), 3.27-3.13 (m, 1H), 2.97 (t, J=6.3 Hz, 2H), 2.03 (s, 3H), 1.26 (d, J=7.5 Hz, 6H).

EXAMPLE 8

[3-(2-{5-ethyl-2-[4-(trifluoromethyl)piperidin-1-yl]-1,3-thiazol-4-yl}ethoxy)-4-methylphenyl]acetic acid:

TLC: Rf 0.54 (chloroform:methanol=8:1);
$^1$H NMR (DMSO-d$_6$): δ 12.22 (brs, 1H), 7.01 (d, J=7.2 Hz, 1H), 6.81 (s, 1H), 6.69 (d, J=7.2 Hz, 1H), 4.12 (t, J=6.3 Hz, 2H), 3.98-3.78 (m, 2H), 3.47 (s, 2H), 3.06-2.76 (m, 4H), 2.63 (q, J=7.2 Hz, 2H), 2.54 (m, 1H), 2.04 (s, 3H), 1.94-1.76 (m, 2H), 1.60-1.44 (m, 2H), 1.12 (t, J=7.2 Hz, 3H).

EXAMPLE 9

[3-(2-{5-isopropyl-2-[4-(trifluoromethoxy)phenyl]-1,3-oxazol-4-yl}ethoxy)-4-methylphenyl]acetic acid:

TLC: Rf 0.39 (chloroform:methanol=9:1);
$^1$H NMR (DMSO-d$_6$): δ 12.23 (brs, 1H), 8.04-7.99 (m, 2H), 7.48-7.45 (m, 2H), 7.00 (d, J=7.5 Hz, 1H), 6.84 (s, 1H), 6.70-6.67 (m, 1H), 4.19 (t, J=6.3 Hz, 2H), 3.46 (s, 2H), 3.22-3.13 (m, 1H), 2.95 (t, J=6.3 Hz, 2H), 2.03 (s, 3H), 1.25 (d, J=6.9 Hz, 6H).

EXAMPLE 10

[4-methyl-3-(2-{5-pentyl-2-[4-(trifluoromethyl)phenyl]-1,3-oxazol-4-yl}ethoxy)phenyl]acetic acid:

TLC: Rf 0.25 (chloroform:methanol=9:1);
$^1$H NMR (CDCl$_3$): δ 8.07 (d, J=8.1 Hz, 2H), 7.65 (d, J=8.1 Hz, 2H), 7.03 (d, J=7.5 Hz, 1H), 6.75 (s, 1H), 6.74 (d, J=7.5 Hz, 1H), 5.89 (bs, 1H), 4.22 (t, J=6.6 Hz, 2H), 3.55 (s, 2H), 2.99 (t, J=6.6 Hz, 2H), 2.71 (t, J=7.5 Hz, 2H), 2.13 (s, 3H), 1.66 (quintet, J=7.5 Hz, 2H), 1.35 (m, 4H), 0.90 (t, J=6.6 Hz, 3H).

EXAMPLE 11

[4-methyl-3-(2-{5-phenyl-2-[4-(trifluoromethyl)phenyl]-1,3-oxazol-4-yl}ethoxy)phenyl]acetic acid:

TLC: Rf 0.51 (chloroform:methanol=9:1);

$^1$H NMR (DMSO-$d_6$): δ 8.25 (d, J=8.4 Hz, 2H), 7.89 (d, J=8.4 Hz, 2H), 7.85 (d, J=7.5 Hz, 2H), 7.53 (d, J=7.5 Hz, 2H), 7.43 (m, 1H), 6.97 (d, J=7.5 Hz, 1H), 6.89 (s, 1H), 6.69 (d, J=7.5 Hz, 1H), 4.35 (t, J=6.0 Hz, 2H), 3.48 (s, 2H), 3.30 (bs, 1H), 3.29 (t, J=6.0 Hz, 2H), 1.91 (s, 3H).

EXAMPLE 12

[3-(2-{5-methyl-2-[4-(trifluoromethyl)phenyl]-1,3-thiazol-4-yl}ethoxy)phenyl]acetic acid:

TLC: Rf 0.45 (chloroform:methanol=8:1);

$^1$H NMR (DMSO-$d_6$): δ 12.27 (brs, 1H), 8.05 (d, J=8.4 Hz, 2H), 7.81 (d, J=8.4 Hz, 2H), 7.19 (dd, J=8.4, 7.5 Hz, 1H), 6.88-6.74 (m, 3H), 4.28 (t, J=6.6 Hz, 2H), 3.50 (s, 2H), 3.14 (t, J=6.6 Hz, 2H), 2.46 (s, 3H).

EXAMPLE 13

[4-methyl-3-(2-{5-methyl-2-[4-(trifluoromethyl)phenyl]-1,3-thizaol-4-yl}ethoxy)phenyl]acetic acid:

TLC: Rf 0.47 (chloroform:methanol=8:1);

$^1$H NMR (DMSO-$d_6$): δ 12.23 (brs, 1H), 8.05 (d, J=7.8 Hz, 2H), 7.81 (d, J=7.8 Hz, 2H), 7.01 (d, J=7.2 Hz, 1H), 6.86 (s, 1H), 6.70 (d, J=7.2 Hz, 1H), 4.27 (t, J=6.3 Hz, 2H), 3.48 (s, 2H), 3.16 (t, J=6.3 Hz, 2H), 2.46 (s, 3H), 2.02 (s, 3H).

EXAMPLE 14

[4-methyl-3-(2-{5-methyl-2-[4-(trifluoromethoxy)phenyl]-1,3-oxazol-4-yl}ethoxy)phenyl]acetic acid:

TLC: Rf 0.20 (chloroform:methanol=9:1);

$^1$H NMR (CDCl$_3$): δ 7.98 (d, J=9.0 Hz, 2H), 7.24 (d, J=9.0 Hz, 2H), 7.04 (d, J=8.1 Hz, 1H), 6.74 (m, 2H), 4.21 (d, J=6.3 Hz, 2H), 3.56 (s, 2H), 2.98 (d, J=6.3 Hz, 2H), 2.36 (s, 3H), 2.14 (s, 3H).

EXAMPLE 15

[3-(2-{5-isopropyl-2-[4-(trifluoromethoxy)phenyl]-1,3-oxazol-4-yl}ethoxy)phenyl]acetic acid:

TLC: Rf 0.21 (chloroform:methanol=9:1);

$^1$H NMR(CDCl$_3$): δ 8.00 (m, 2H), 7.25 (d, J=8.1 Hz, 2H), 7.19 (t, J=8.1 Hz, 1H), 6.80 (m, 3H), 4.18 (t, J=6.6 Hz, 2H), 3.56 (s, 2H), 3.14 (septet, J=6.9 Hz, 1H), 2.97 (t, J=6.6 Hz, 2H), 1.32 (d, J=6.9 Hz, 6H).

EXAMPLE 16

[3-(2-{5-(2,2,2-trifluoroethyl)-2-[4-(trifluoromethyl)phenyl]-1,3-oxazol-4-yl}ethoxy)phenyl]acetic acid:

TLC: Rf 0.30 (chloroform:methanol=9:1);

$^1$H NMR (DMSO-$d_6$): δ 12.29 (brs, 1H), 8.13 (d, J=8.4 Hz, 2H), 7.90 (d, J=8.4 Hz, 2H), 7.19 (t, J=7.2 Hz, 1H), 6.82-6.79 (m, 3H), 4.23-4.04 (m, 4H), 3.50 (s, 2H), 3.06 (t, J=6.3 Hz, 2H).

EXAMPLE 17

[3-(2-{5-propyl-2-[4-(trifluoromethoxy)phenyl]-1,3-oxazol-4-yl}ethoxy)phenyl]acetic acid:

TLC: Rf 0.27 (chloroform:methanol=9:1);

$^1$H NMR (CDCl$_3$): δ 8.00 (m, 2H), 7.27-7.18 (m, 3H), 6.86-6.78 (m, 3H), 4.21 (t, J=6.6 Hz, 2H), 3.59 (s, 2H), 2.97 (t, J=6.6 Hz, 2H), 2.68 (t, J=7.5 Hz, 2H), 1.74 (sixtet, J=7.5 Hz, 2H), 0.99 (t, J=7.5 Hz, 3H).

EXAMPLE 18

[4-methyl-3-(2-{5-propyl-2-[4-(trifluoromethoxy)phenyl]-1,3-oxazol-4-yl}ethoxy)phenyl]acetic acid:

TLC: Rf 0.21 (chloroform:methanol=9:1);

$^1$H NMR (CDCl$_3$): δ 8.00 (m, 2H), 7.24 (m, 2H), 7.05 (d, J=7.5 Hz, 1H), 6.77 (s, 1H), 6.75 (d, J=7.5 Hz, 1H), 4.23 (t, J=6.3 Hz, 2H), 3.58 (s, 2H), 2.99 (t, J=6.3 Hz, 2H), 2.69 (t, J=7.2 Hz, 2H), 2.14 (s, 3H), 1.71 (sixtet, J=7.2 Hz, 2H), 0.99 (t, J=7.5 Hz, 3H).

EXAMPLE 19

[3-(2-{5-butyl-2-[4-(trifluoromethoxy)phenyl]-1,3-oxazol-4-yl}ethoxy)phenyl]acetic acid:

TLC: Rf 0.31 (chloroform:methanol=9:1);

$^1$H NMR (CDCl$_3$): δ 8.00 (m, 2H), 7.27-7.19 (m, 3H), 6.86-6.78 (m, 3H), 4.21 (t, J=6.6 Hz, 2H), 3.59 (s, 2H), 2.97 (t, J=6.6 Hz, 2H), 2.70 (t, J=7.5 Hz, 2H), 1.66 (quintet, J=7.5 Hz, 2H), 1.40 (sixtet, J=7.5 Hz, 2H), 0.95 (t, J=7.5 Hz, 3H).

EXAMPLE 20

[3-(2-{5-butyl-2-[4-(trifluoromethoxy)phenyl]-1,3-oxazol-4-yl}ethoxy)-4-methylphenyl]acetic acid:

TLC: Rf 0.35 (chloroform:methanol=9:1);

$^1$H NMR (CDCl$_3$): δ 7.93 (d, J=8.7 Hz, 2H), 7.17 (d, J=8.7 Hz, 2H), 6.89 (d, J=7.5 Hz, 1H), 6.68 (s, 1H), 6.61 (d, J=7.5 Hz, 1H), 4.54 (bs, 1H), 4.11 (t, J=6.3 Hz, 2H), 3.43 (s, 2H), 2.88 (t, J=6.3 Hz, 2H), 2.66 (t, J=7.2 Hz, 2H), 2.06 (s, 3H), 1.60 (quintet, J=7.2 Hz, 2H), 1.36 (sixtet, J=7.2 Hz, 2H), 0.92 (t, J=7.2 Hz, 3H).

EXAMPLE 21

[4-ethyl-3-(2-{5-methyl-2-[4-(trifluoromethyl)phenyl]-1,3-oxazol-4-yl}ethoxy)phenyl]acetic acid:

TLC: Rf 0.41 (chloroform:methanol=8:1);

$^1$H NMR (DMSO-$d_6$): δ 12.24 (brs, 1H), 8.09 (d, J=8.1 Hz, 2H), 7.84 (d, J=8.1 Hz, 2H), 7.00 (d, J=7.5 Hz, 1H), 6.85 (s, 1H), 6.72 (d, J=7.5 Hz, 1H), 4.19 (t, J=6.3 Hz, 2H), 3.48 (s, 2H), 2.96 (t, J=6.3 Hz, 2H), 2.44 (q, J=7.5 Hz, 2H), 2.38 (s, 3H), 0.98 (t, J=7.5 Hz, 3H).

EXAMPLE 22

(3-{2-[2-(2,2-difluoro-1,3-benzodioxol-5-yl)-5-methyl-1,3-oxazol-4-yl]ethoxy}-4-methylphenyl)acetic acid:

TLC: Rf 0.31 (chloroform:methanol=9:1);

$^1$H NMR (DMSO-$d_6$): δ 7.84 (s, 1H), 7.76 (d, J=8.4 Hz, 1H), 7.51 (d, J=8.4 Hz, 1H), 7.00 (d, J=7.5 Hz, 1H), 6.83 (s, 1H), 6.69 (d, J=7.5 Hz, 1H), 4.16 (t, J=6.3 Hz, 2H), 3.46 (s, 2H), 2.92 (t, J=6.3 Hz, 2H), 2.34 (s, 3H), 2.04 (s, 3H).

EXAMPLE 23

(3-{2-[2-(2,2-difluoro-1,3-benzodioxol-5-yl)-5-propyl-1,3-oxazol-4-yl]ethoxy}phenyl)acetic acid:

TLC: Rf 0.30 (chloroform:methanol=9:1);
$^1$H NMR (DMSO-$d_6$): δ 7.85 (s, 1H), 7.77 (dd, J=8.1, 0.9 Hz, 1H), 7.51 (dd, J=8.1, 0.9 Hz, 1H), 7.18 (dd, J=7.5, 7.5 Hz, 1H), 6.79 (m, 3H), 4.18 (t, J=6.6 Hz, 2H), 3.49 (s, 2H), 2.92 (t, J=6.6 Hz, 2H), 2.69 (t, J=7.2 Hz, 2H), 1.65 (sixtet, J=7.2 Hz, 2H), 0.93 (t, J=7.2 Hz, 3H).

EXAMPLE 24

(3-{2-[2-(2,2-difluoro-1,3-benzodioxol-5-yl)-5-propyl-1,3-oxazol-4-yl]ethoxy}-4-methylphenyl)acetic acid:

TLC: Rf 0.33 (chloroform:methanol=9:1);
$^1$H NMR (DMSO-$d_6$): δ 7.84 (d, J=1.5 Hz, 1H), 7.77 (dd, J=8.4, 1.5 Hz, 1H), 7.51 (d, J=8.4 Hz, 1H), 7.01 (d, J=7.5 Hz, 1H), 6.85 (s, 1H), 6.70 (d, J=7.5 Hz, 1H), 4.19 (t, J=6.3 Hz, 2H), 3.48 (s, 2H), 2.94 (t, J=6.3 Hz, 2H), 2.68 (t, J=7.2 Hz, 2H), 2.30 (s, 3H), 1.64 (sixtet, J=7.2 Hz, 2H), 0.92 (t, J=7.2 Hz, 3H).

EXAMPLE 25

(3-{2-[2-(2,2-difluoro-1,3-benzodioxol-5-yl)-5-isopropyl-1,3-oxazol-4-yl]ethoxy}phenyl)acetic acid:

TLC: Rf 0.25 (chloroform:methanol=9:1);
$^1$H NMR (DMSO-$d_6$): δ 7.87 (d, J=0.9 Hz, 1H), 7.78 (dd, J=8.4, 0.9 Hz, 1H), 7.52 (d, J=8.4 Hz, 1H), 7.18 (dd, J=7.8, 7.8 Hz, 1H), 6.79 (m, 3H), 4.17 (t, J=6.6 Hz, 2H), 3.50 (s, 2H), 3.18 (septet, J=6.9 Hz, 2H), 2.93 (t, J=6.6 Hz, 2H), 1.27 (d, J=6.9 Hz, 2H).

EXAMPLE 26

(3-{2-[2-(2,2-difluoro-1,3-benzodioxol-5-yl)-5-isopropyl-1,3-oxazol-4-yl]ethoxy}-4-methylphenyl)acetic acid:

TLC: Rf 0.37 (chloroform:methanol=9:1);
$^1$H NMR (DMSO-$d_6$): δ 7.87 (d, J=1.8 Hz, 1H), 7.78 (dd, J=8.4, 1.8 Hz, 1H), 7.52 (d, J=8.4 Hz, 1H), 7.01 (d, J=7.5 Hz, 1H), 6.84 (s, 1H), 6.69 (d, J=7.5 Hz, 1H), 4.19 (t, J=6.3 Hz, 2H), 3.48 (s, 2H), 3.18 (septet, J=6.9 Hz, 1H), 2.95 (t, J=6.3 Hz, 2H), 2.04 (s, 3H), 1.26 (d, J=6.9 Hz, 6H).

EXAMPLE 27

(3-{2-[2-(2,2-difluoro-1,3-benzodioxol-5-yl)-5-ethyl-1,3-oxazol-4-yl]ethoxy}-4-methylphenyl)acetic acid:

TLC: Rf 0.26 (chloroform:methanol=9:1);
$^1$H NMR (DMSO-$d_6$): δ 7.86 (d, J=1.8 Hz, 1H), 7.78 (dd, J=8.4, 1.8 Hz, 1H), 7.52 (d, J=8.4 Hz, 1H), 7.01 (d, J=7.5 Hz, 1H), 6.84 (s, 1H), 6.69 (d, J=7.5 Hz, 1H), 4.18 (t, J=6.3 Hz, 2H), 3.48 (s, 2H), 2.94 (t, J=6.3 Hz, 2H), 2.73 (q, J=7.5 Hz, 2H), 2.04 (s, 3H), 1.21 (t, J=7.5 Hz, 3H).

EXAMPLE 28

4-(trifluoromethyl)piperidine hydrochloride:

Under atmosphere of argon, a solution of 4-(trifluoromethyl)pyridine (9.33 g) in methanol (80 mL) was added by concentrated hydrochloric acid (16 mL) and platinum oxide (510 mg) and stirred for three days at room temperature under hydrogen pressure. The reaction mixture was filtrated by celite (trade name) and the filtrate was concentrated. The residue was added by saturated sodium dicarbonate aqueous solution and extracted by ethyl acetate. The organic layer was washed with saturated brine, dried over anhydrous magnesium sulfate and then filtrated. The filtrate was added by 4N hydrogen chloride/ethyl acetate solution (50 mL) and then concentrated to give the title compound (13.0 g) having the following physical data.

TLC: Rf 0.13 (chloroform:methanol=10:1);
$^1$H NMR (CDCl$_3$): δ 1.72 (dd, J=13.0, 4.0 Hz, 1H), 1.81 (dd, J=13.0, 4.0 Hz, 1H), 2.05-2.20 (m, 2H), 2.41-2.80 (m, 1H), 3.06 (dt, J=13.0, 3.0 Hz, 2H), 3.40-3.60 (m, 2H).

EXAMPLE 29

4-(trifluoromethyl)-1-piperidinecarbothioamide:

A suspended solution of the compound prepared in Example 28 (3.80 g) in tetrahydrofuran (25 mL) was added by triethylamine (2.9 mL) and thiocarbodiimidazole (3.80 g) and stirred overnight at room temperature. The reaction mixture was poured with water and extracted by ethyl acetate. The organic layer was washed with saturated brine, dried over anhydrous magnesium sulfate and then concentrated to give brown oily matter. A mixed solution of this oily matter in ethanol (30 mL) and tetrahydrofuran (15 mL) was cooled by iced water, saturated by bubbling ammonia gas and then stirred overnight at room temperature. The reaction mixture was concentrated, the obtained yellow solid was washed with diethylether and dried over to give the title compound (2.19 g) having the following physical data.

TLC: Rf 0.47 (chloroform:methanol=10:1);
$^1$H NMR (CDCl$_3$): δ 1.76-1.61 (m, 2H), 2.03-1.93 (m, 2H), 2.44-2.24 (m, 1H), 3.15-3.03 (m, 2H), 4.65 (brd, J=13.0 Hz, 2H), 5.83 (brs, 2H).

EXAMPLE 30 methyl {5-methyl-2-[4-(trifluoromethyl)piperidin-1-yl]-1,3-thiazol-4-yl}acetate:

A solution of the compound prepared in Example 29 (2.18 g) in ethanol (10 mL) was added by methyl 4-bromo-3-oxopentanoate (2.37 g) and stirred overnight at room temperature. The reaction mixture was added by water and saturated sodium dicarbonate aqueous solution and extracted by ethyl acetate. The organic layer was washed with saturated brine, dried over anhydrous magnesium sulfate and then concentrated. The residue was purified by column chromatography on silica gel (hexane:ethyl acetate=from 4:2 to 2:1) to give the title compound (2.86 g) having physical data (2.86 g).

TLC: Rf 0.51 (hexane:ethyl acetate=2:1);
$^1$H NMR (CDCl$_3$): δ 1.67 (dq, J=5.0, 13.0 Hz, 2H), 1.93 (brd, J=13.0 Hz, 2H), 2.23 (s, 3H), 2.31-2.11 (m, 1H), 2.89 (dt, J=2.5, 13.0 Hz, 2H), 3.53 (s, 2H), 3.70 (s, 3H), 4.00 (brd, J=13.0 Hz, 2H).

EXAMPLE 31

2-{5-methyl-2-[4-(trifluoromethyl)piperidin-1-yl]-1,3-thiazol-4-yl}ethanol:

A solution of lithium aluminum hydride (336 mg) in anhydrous tetrahydrofuran (35 mL) was cooled by iced water, dropped by a solution of the compound prepared in Example 30 (2.85 g) in anhydrous tetrahydrofuran (5 mL) and stirred for 15 minutes at room temperature. The reaction mixture was kept cooling down by iced water, dropped by saturated sodium sulfate (1.8 mL) and stirred for an hour at room temperature. The reaction mixture was added by diethylether (20 mL), stirred, dried over anhydrous magnesium sulfate and then filtrated with celite. The filtrate was concentrated to give the title compound (2.46 g) having the following physical data.

TLC: Rf 0.24 (hexane:ethyl acetate=2:1);

$^1$H NMR (CDCl$_3$): δ 1.68 (dq, J=4.5, 13.0 Hz, 2H), 2.00-1.90 (m, 2H), 2.21 (s, 3H), 2.33-2.13 (m, 1H), 2.67 (t, J=5.5 Hz, 2H), 2.92 (dt, J=3.0, 13.0 Hz, 2H), 3.85 (t, J=5.5 Hz, 2H), 3.98 (brd, J=13.2 Hz, 2H), 4.29 (br, 1H).

EXAMPLE 32 methyl [2-fluoro-3-(2-{5-methyl-2-[4-(trifluoromethyl)piperidin-1-yl]-1,3-thiazol-4-yl}ethoxy)phenyl]acetate:

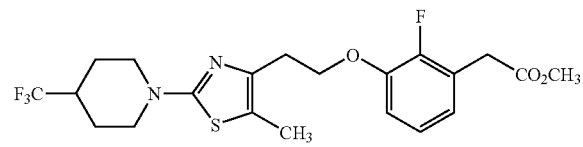

Under atmosphere of argon, a solution of the compound prepared in Example 31 (227 mg), methyl (2-fluoro-3-hydroxyphenyl)acetate (184 mg) and triphenylphosphine (262 mg) in anhydrous dichloromethane (5 mL) was dropped by diethyl azodicarboxylate (435 mg) and stirred for 4 hours at room temperature. The reaction mixture was concentrated and the obtained residue was purified by column chromatography on silica gel (hexane:ethyl acetate=from 9:1 to 7:3) to give the title compound (306 mg) having the following physical data.

TLC: Rf 0.64 (hexane:ethyl acetate=1:2);

$^1$H NMR (CDCl$_3$): δ 1.68 (qd, J=12.7, 4.4 Hz, 2H), 1.94 (d, J=12.7 Hz, 2H), 2.13-2.28 (m, 1H), 2.26 (s, 3H), 2.89 (td, J=12.7, 2.7 Hz, 2H), 2.98 (t, J=6.9 Hz, 2H), 3.65-3.68 (m, 2H), 3.70 (s, 3H), 4.01 (d, J=12.7 Hz, 2H), 4.25 (t, J=6.9 Hz, 2H), 6.74-6.83 (m, 1H), 6.85-7.02 (m, 2H).

EXAMPLE 33

[2-fluoro-3-(2-{5-methyl-2-[4-(trifluoromethyl)piperidin-1-yl]-1,3-thiazol-4-yl}ethoxy)phenyl]acetic acid:

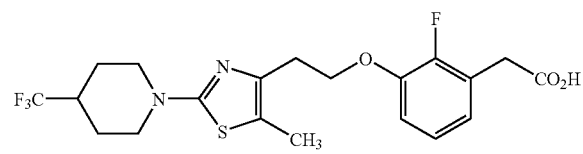

A mixed solution of the compound prepared in Example 32 (306 mg) in methanol (5 mL) and tetrahydrofuran (5 mL) was added by 5N sodium hydroxide aqueous solution (2.00 mL) at room temperature and stirred for 2 hours. The reaction mixture was adjusted to pH4 by 2N hydrochloric acid, diluted with water and then the obtained crystal was divided by filtration. The crystal was washed with water and dried over to give the title compound (226 mg) having the following physical data.

TLC: Rf 0.60 (chloroform:methanol=9:1);

$^1$H NMR (DMSO-d$_6$): δ 1.47 (qd, J=12.7, 4.4 Hz, 2H), 1.86 (d, J=11.5 Hz, 2H), 2.19 (s, 3H), 2.47-2.63 (m, 1H), 2.86 (t, J=6.7 Hz, 2H), 2.94 (dt, J=12.7, 2.7 Hz, 2H), 3.57 (d, J=1.5 Hz, 2H), 3.86 (d, J=12.7 Hz, 2H), 4.20 (t, J=6.7 Hz, 2H), 6.80-6.87 (m, 1H), 6.97-7.09 (m, 2H), 12.20-12.70 (brs, 1H).

EXAMPLE 34-EXAMPLE 34(15)

By the same procedure as Example 32 and Example 33 using the compound prepared in Example 31 or the corresponding alcohol derivative instead thereof and methyl (2-fluoro-3-hydroxyphenyl)acetate or the corresponding alcohol derivative instead thereof, the following compound of the present invention was obtained.

EXAMPLE 34

(3-{2-[2-(1,1'-biphenyl-4-yl)-5-methyl-1,3-oxazol-4-yl]ethoxy}-4-methylphenyl)acetic acid:

TLC: Rf 0.57 (dichloromethane:methanol=9:1);

$^1$H NMR (DMSO-d$_6$): δ 2.06 (s, 3H), 2.35 (s, 3H), 2.94 (t, J=6.23 Hz, 2H), 3.49 (s, 2H), 4.19 (t, J=6.23 Hz, 2H), 6.71 (d, J=7.57 Hz, 1H), 6.86 (s, 1H), 7.02 (d, J=7.57 Hz, 1H), 7.38 (t, J=7.57 Hz, 1H), 7.47 (t, J=7.57 Hz, 2H), 7.70 (d, J=7.57 Hz, 2H), 7.78 (d, J=8.30 Hz, 2H), 7.98 (d, J=8.30 Hz, 2H), 12.25 (s, 1H).

EXAMPLE 34(1)

(4-methyl-3-{2-[5-methyl-2-(4-phenylpiperidin-1-yl)-1,3-thiazol-4-yl]ethoxy}phenyl)acetic acid:

TLC: Rf 0.65 (methanol:dichloromethane=1:9);

$^1$H NMR (DMSO-d$_6$): δ 12.23(brs, 1H), 7.34-7.13(m, 5H), 7.02(d, J=7.5 Hz, 1H), 6.82(d, J=1.2 Hz, 1H), 6.79(dd, J=7.5, 1.2 Hz, 1H), 4.12(t, J=6.3 Hz, 2H), 3.96-3.83(m, 2H), 3.48(s, 2H), 2.99(dt, J=12.3, 2.7 Hz, 2H), 2.86(t, J=6.3 Hz, 2H), 2.78-2.62(m, 1H), 2.20(s, 3H), 2.05(s, 3H), 1.87-1.76(m, 2H), 1.67(dq, J=12.3, 3.9 Hz, 2H).

EXAMPLE 34(2)

(3-{2-[2-(4-chlorophenyl)-5-methyl-1,3-oxazol-4-yl]ethoxy}-4-methylphenyl)acetic acid:

TLC: Rf 0.31 (chloroform:methanol=9:1);

$^1$H NMR (DMSO-d$_6$): δ 2.04 (s, 3H), 2.34 (s, 3H), 2.93 (t, J=6.3 Hz, 2H), 3.48 (s, 2H), 4.17 (t, J=6.3 Hz, 2H), 6.70 (dd, J=7.5, 1.5 Hz, 1H), 6.84 (d, J=1.5 Hz, 1H), 7.01 (dd, J=7.5, 0.7 Hz, 1H), 7.54 (d, J=9.0 Hz, 2H), 7.90 (d, J=9.0 Hz, 2H), 12.22 (s, 1H).

EXAMPLE 34(3)

(2-fluoro-3-{2-[5-methyl-2-(4-phenylpiperidin-1-yl)-1,3-thiazol-4-yl]ethoxy}phenyl)acetic acid:

TLC: Rf 0.54 (chloroform:methanol=9:1);

$^1$H NMR (DMSO-d$_6$): δ 1.67 (qd, J=12.3, 4.2 Hz, 2H), 1.81 (t, J=12.3 Hz, 2H), 2.20 (s, 3H), 2.71 (tt, J=8.4, 3.6 Hz, 1H), 2.87 (t, J=6.6 Hz, 2H), 3.00 (td, J=12.3, 2.1 Hz, 2H), 3.58 (s, 2H), 3.90 (d, J=12.3 Hz, 2H), 4.21 (t, J=6.6 Hz, 2H), 6.73-6.89 (m, 1H), 6.93-7.13 (m, 2H), 7.13-7.35 (m, 5H), 12.37 (s, 1H).

EXAMPLE 34(4)

(3-{2-[5-methyl-2-(4-phenylpiperazin-1-yl)-1,3-thiazol-4-yl]ethoxy}phenyl)acetic acid:

TLC: Rf 0.54 (methanol:dichloromethane=1:9);

$^1$H NMR (DMSO-$d_6$): δ 12.25(brs, 1H), 7.28-7.13(m, 3H), 6.96(d, J=9.0 Hz, 2H), 6.86-6.75(m, 4H), 4.14(t, J=6.9 Hz, 2H), 3.51(s, 2H), 3.48-3.39(m, 4H), 3.26-3.15(m, 4H), 2.86(t, J=6.9 Hz, 2H), 2.21(s, 3H).

EXAMPLE 34(5)

[3-(2-{2-[4-(4-chlorophenyl)piperazin-1-yl]-5-methyl-1,3-thiazol-4-yl}ethoxy)phenyl]acetic acid:

TLC: Rf 0.51 (methanol:dichloromethane=1:9);

$^1$H NMR (DMSO-$d_6$): δ 12.25(brs, 1H), 7.24(d, J=9.0 Hz, 2H), 7.19(t, J=8.1 Hz, 1H), 6.97(d, J=9.0 Hz, 2H), 6.84-6.75 (m, 3H), 4.14(t, J=6.9 Hz, 2H), 3.51(s, 2H), 3.48-3.39(m, 4H), 3.27-3.15(m, 4H), 2.86(t, J=6.9 Hz, 2H), 2.21(s, 3H).

EXAMPLE 34(6)

[3-(2-{5-methyl-2-[4-(4-methylphenyl)piperazin-1-yl]-1,3-thiazol-4-yl}ethoxy)phenyl]acetic acid:

TLC: Rf 0.48 (methanol:dichloromethane=1:9);

$^1$H NMR (DMSO-$d_6$): δ 12.26(brs, 1H), 7.18(t, J=8.1 Hz, 1H), 7.04(d, J=8.4 Hz, 2H), 6.86(d, J=8.4 Hz, 2H), 6.84-6.75 (m, 3H), 4.14(t, J=6.9 Hz, 2H), 3.51(s, 2H), 3.48-3.38(m, 4H), 3.21-3.08(m, 4H), 2.86(t, J=6.9 Hz, 2H), 2.21(s, 3H), 2.20(s, 3H).

EXAMPLE 34(7)

(3-{2-[2-(1,3-dihydro-2H-isoindole-2-yl)-5-methyl-1,3-thiazol-4-yl]ethoxy}-2-fluorophenyl)acetic acid:

TLC: Rf 0.52 (chloroform:methanol=9:1);

$^1$H NMR (DMSO-$d_6$): δ 2.23 (s, 3H), 2.91 (t, J=6.6 Hz, 2H), 3.58 (d, J=0.9 Hz, 2H), 4.24 (t, J=6.6 Hz, 2H), 4.66 (s, 4H), 6.80-6.87 (m, 1H), 6.98-7.10 (m, 2H), 7.27-7.34 (m, 2H), 7.35-7.41 (m, 2H), 12.41 (brs, 1H).

EXAMPLE 34(8)

[3-(2-{2-[4-(4-chlorophenyl)piperazin-1-yl]-5-methyl-1,3-thiazol-4-yl}ethoxy)-2-fluorophenyl]acetic acid:

TLC: Rf 0.56 (methanol:dichloromethane=1:9);

$^1$H NMR (DMSO-$d_6$): δ 12.41(brs, 1H), 7.24(d, J=9.0 Hz, 2H), 7.09-6.92(m, 4H), 6.88-6.78(m, 4H), 4.21(t, J=6.6 Hz, 2H), 3.57(d, J=1.5 Hz, 2H), 3.48-3.37(m, 4H), 3.28-3.16(m, 4H), 2.88(t, J=6.6 Hz, 2H), 2.21(s, 3H).

EXAMPLE 34(9)

[3-(2-{2-[4-(4-chlorophenyl)piperazin-1-yl]-5-methyl-1,3-thiazol-4-yl}ethoxy)-4-methylphenyl]acetic acid:

TLC: Rf 0.48 (methanol:dichloromethane=1:9);

$^1$H NMR (DMSO-$d_6$): δ 12.21(brs, 1H), 7.24(d, J=9.0 Hz, 2H), 7.01(d, J=7.5 Hz, 1H), 6.97(d, J=9.0 Hz, 2H), 6.81-6.78 (d, J=1.2 Hz, 1H), 6.69(dd, J=7.5, 1.2 Hz, 1H), 4.13(t, J=6.6 Hz, 2H), 3.48(s, 2H), 3.46-3.37(m, 4H), 3.26-3.15(m, 4H), 2.87(t, J=6.6 Hz, 2H), 2.21(s, 3H), 2.05(s, 3H).

EXAMPLE 34(10)

[3-(2-{2-[4-(4-chlorophenyl)piperidin-1-yl]-5-methyl-1,3-thiazol-4-yl}ethoxy)-4-methylphenyl]acetic acid:

TLC: Rf 0.40 (chloroform:methanol=9:1);

$^1$H NMR (DMSO-$d_6$): δ 1.55-1.64 (m, J=12.5, 4.0 Hz, 1H), 1.68 (dd, J=12.5, 4.0 Hz, 1H), 1.74-1.87 (m, 2H), 2.05 (s, 3H), 2.20 (s, 3H), 2.73 (tt, J=12.5, 3.5 Hz, 1H), 2.85 (t, J=6.5 Hz, 2H), 2.99 (dt, J=12.5, 2.5 Hz, 2H), 3.48 (s, 2H), 3.89 (brd, J=12.5 Hz, 2H), 4.12 (t, J=6.5 Hz, 2H), 6.69 (dd, J=7.0, 1.1 Hz, 1H), 6.82 (d, J=1.1 Hz, 1H), 7.02 (d, J=7.5 Hz, 1H), 7.27 (d, J=8.5 Hz, 2H), 7.34 (d, J=8.5 Hz, 2H), 12.20 (brs, 1H).

EXAMPLE 34(11)

(3-{2-[2-(3,4-dihydro-1H-isoquinolin-2-yl)-5-methyl-1,3-thiazol-4-yl]ethoxy}-4-methylphenyl)acetic acid:

TLC: Rf 0.55 (methanol:dichloromethane=1:9);

$^1$H NMR (DMSO-$d_6$): δ 12.20(brs, 1H), 7.26-7.12(m, 4H), 7.02(d, J=7.5 Hz, 1H), 6.82(d, J=1.5 Hz, 1H), 6.69(dd, J=7.5, 1.5 Hz, 1H), 4.51(s, 2H), 4.14(t, J=6.6 Hz, 2H), 3.61(t, J=6.0 Hz, 2H), 3.48(s, 2H), 2.95-2.82(m, 4H), 2.22(s, 3H), 2.05(s, 3H).

EXAMPLE 34(12)

(4-methyl-3-{2-[5-methyl-2-(4-phenyl-3,6-dihydro-2H-pyridin-1-yl)-1,3-thiazol-4-yl]ethoxy}phenyl)acetic acid:

TLC: Rf 0.52 (chloroform:methanol=9:1);

$^1$H NMR (CDCl$_3$): δ 2.15 (s, 3H), 2.27 (s, 3H), 2.61-2.68 (m, 2H), 2.98 (t, J=6.6 Hz, 2H), 3.58 (s, 2H), 3.68 (t, J=5.8 Hz, 2H), 4.02-4.07 (m, 2H), 4.20 (t, J=6.6 Hz, 2H), 6.06-6.11 (m, 1H), 6.72-6.79 (m, 2H), 7.05 (d, J=7.5 Hz, 1H), 7.21-7.43 (m, 5H).

EXAMPLE 34(13)

[3-(2-{2-[4-(4-fluorophenyl)piperidin-1-yl]-5-methyl-1,3-thiazol-4-yl}ethoxy)-4-methylphenyl]acetic acid:

TLC: Rf 0.38 (methanol:dichloromethane=1:9);

$^1$H NMR (DMSO-$d_6$): δ 12.21(brs, 1H), 7.27(dd, J=8.7, 5.7 Hz, 2H), 7.10(t, J=8.7 Hz, 2H), 7.02(d, J=7.5 Hz, 1H), 6.82(d, J=1.2 Hz, 1H), 6.70(dd, J=7.5, 1.2 Hz, 1H), 4.12(t, J=6.6 Hz, 2H), 3.96-3.82(m, 2H), 3.48(s, 2H), 2.98(t, J=dt, 12.3, 2.4 Hz, 2H), 2.86(t, J=6.6 Hz, 2H), 2.72(tt, J=12.3, 3.3 Hz, 1H), 2.20(s, 3H), 2.05(s, 3H), 1.87-1.73(m, 2H), 1.64(dq, J=12.3, 4.2 Hz, 2H).

EXAMPLE 34(14)

(4-methyl-3-{2-[5-methyl-2-(4-phenylpiperazin-1-yl)-1,3-thiazol-4-yl]ethoxy}phenyl)acetic acid:

TLC: Rf 0.54 (chloroform:methanol=9:1);

$^1$H NMR (CDCl$_3$): δ 2.14 (s, 3H), 2.26 (s, 3H), 2.96 (t, J=6.6 Hz, 2H), 3.21-3.27 (m, 4H), 3.49-3.58 (m, 6H), 4.17 (t, J=6.6 Hz, 2H), 6.72-6.76 (m, 2H), 6.86-6.97 (m, 3H), 7.04 (dd, J=8.1, 0.7 Hz, 1H), 7.24-7.31 (m, 2H).

EXAMPLE 34(15)

{4-methyl-3-[2-(5-methyl-2-{4-[5-(trifluoromethyl)pyridin-2-yl]piperazin-1-yl}-1,3-thiazol-4-yl)ethoxy]phenyl}acetic acid:

TLC: Rf 0.47 (methanol:dichloromethane=1:9);

$^1$H NMR (CDCl$_3$): δ 8.44-8.38(m, 1H), 7.65(dd, J=9.0, 2.4 Hz, 1H), 7.04(d, J=7.2 Hz, 1H), 6.80-6.71(m, 2H), 6.65(d,

J=9.0 Hz, 1H), 4.19(t, J=6.6 Hz, 2H), 3.79-3.69(m, 4H), 3.57(s, 2H), 3.54-3.46(m, 4H), 2.96(t, J=6.6 Hz, 2H), 2.27(s, 3H), 2.14(s, 3H).

EXAMPLE 35 methyl (3-{2-[2-(4-bromophenyl)-5-methyl-1,3-oxazol-4-yl]ethoxy}-4-methylphenyl)acetate:

By the same procedure as Example 31 and Example 32 using [2-(4-bromophenyl)-5-methyl-1,3-oxazol-4-yl]acetate instead of the compound prepared in Example 30 and methyl (3-hydroxy-4-methylphenyl)acetate instead of methyl(2-fluoro-3-hydroxyphenyl)acetate, the title compound having the following physical data was obtained.

TLC: Rf 0.48 (ethyl acetate:hexane=1:2);

$^1$H NMR (CDCl$_3$): δ 2.15 (s, 3H), 2.37 (s, 3H), 2.98 (t, J=6.3 Hz, 2H), 3.56 (s, 2H), 3.67 (s, 3H), 4.23 (t, J=6.3 Hz, 2H), 6.78-6.71 (m, 2H), 7.05 (d, J=7.8 Hz, 1H), 7.56 (d, J=8.7 Hz, 2H), 7.84 (d, J=8.7 Hz, 2H).

EXAMPLE 36 methyl [4-methyl-3-(2-{5-methyl-2-[4-(pyridin-2-yl)phenyl]-1,3-oxazol-4-yl}ethoxy)phenyl]acetate:

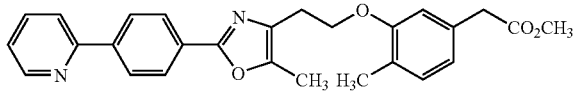

Under atmosphere of argon, a solution of the compound prepared in Example 35 (300 mg), tri n-butyl(2-pyridyl)tin (273 mg), lithium chloride (85 mg) and tetrakis(triphenylphosphine)palladium (39 mg) in dioxane (3 mL) was stirred for 5 hours at 115° C. The reaction mixture was cooled down at room temperature, diluted with water and extracted by ethyl acetate. The organic layer was washed with water and saturated brine successively, dried over anhydrous magnesium sulfate and then concentrated. The residue was purified by column chromatography on silica gel (hexane:ethyl acetate=2:1) to give the title compound (240 mg) having the following physical data.

TLC: Rf 0.09 (hexane:ethyl acetate=2:1).

EXAMPLE 37 methyl [3-(2-{2-[4-(furan-3-yl)phenyl]-5-methyl-1,3-oxazol-4-yl}ethoxy)-4-methylphenyl]acetate:

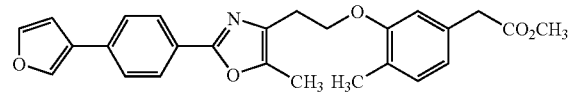

A mixed solution of the compound prepared in Example 35 (300 mg), 3-furylborane acid (97 mg), sodium carbonate (92 mg) and tetrakis(triphenylphospine)palladium (39 mg) in dimethoxyethane (6 mL) and water (2 mL) was stirred for 2 hours at 90° C. The reaction mixture was diluted with water and extracted by ethyl acetate. The organic layer was washed with water and saturated brine successively, dried over anhydrous magnesium sulfate and then concentrated. The residue was purified by column chromatography on silica gel (hexane:ethyl acetate=from 9:1 to 4:1) to give the title compound (260 mg) having the following physical data.

TLC: Rf 0.24 (hexane:ethyl acetate=2:1).

EXAMPLE 38-EXAMPLE 38(1)

By the same procedure as Example 33 using the compound prepared in Example 36 and Example 37 instead of the compound prepared in Example 32, the following compounds of the present invention were obtained.

EXAMPLE 38

[4-methyl-3-(2-{5-methyl-2-[4-(pyridin-2-yl)phenyl]-1,3-oxazol-4-yl}ethoxy)phenyl]acetic acid:

TLC: Rf 0.38 (chloroform:methanol=9:1);

$^1$H NMR (DMSO-d$_6$): δ 2.05 (s, 3H), 2.37 (s, 3H), 2.95 (t, J=6.32 Hz, 2H), 3.45 (s, 2H), 4.18 (t, J=6.32 Hz, 2H), 6.69 (d, J=7.51 Hz, 1H), 6.86 (s, 1H), 7.01 (d, J=7.51 Hz, 1H), 7.38 (ddd, J=7.50, 4.76, 1.10 Hz, 1H), 7.90 (ddd, J=8.06, 7.50, 1.74 Hz, 1H), 8.01 (d, J=8.24 Hz, 2H), 8.01-8.05 (m, 1H), 8.22 (d, J=8.24 Hz, 2H), 8.68 (ddd, J=4.76, 1.74, 0.91 Hz, 1H).

EXAMPLE 38(1)

[3-(2-{2-[4-(furan-3-yl)phenyl]-5-methyl-1,3-oxazol-4-yl}ethoxy)-4-methylphenyl]acetic acid:

TLC: Rf 0.33 (chloroform:methanol=9:1);

$^1$H NMR (DMSO-d$_6$): δ 2.06 (s, 3H), 2.35 (s, 3H), 2.93 (t, J=6.32 Hz, 2H), 3.49 (s, 2H), 4.17 (t, J=6.32 Hz, 2H), 6.70 (d, J=7.51 Hz, 1H), 6.85 (s, 1H), 7.02 (d, J=7.51 Hz, 1H), 7.01-7.02 (m, 1H), 7.73 (d, J=8.24 Hz, 2H), 7.75-7.78 (m, 1H), 7.90 (d, J=8.24 Hz, 2H), 8.28 (s, 1H), 12.25 (brs, 1H).

EXAMPLE 39-EXAMPLE 39(8)

By the same procedure as Example 37 and Example 33 using the compound prepared in Example 35 or the corresponding derivative instead thereof and the corresponding borane acid instead of 3-furylborane acid, the following compounds of the present invention were obtained.

EXAMPLE 39

(3-{2-[2-(4'-fluoro-1,1'-biphenyl-4-yl)-5-methyl-1,3-oxazol-4-yl]ethoxy}-4-methylphenyl)acetic acid:

TLC: Rf 0.54 (methanol:dichloromethane=1:9);

$^1$H NMR (DMSO-d$_6$): δ 12.24(brs, 1H), 7.97(d, J=8.4 Hz, 2H), 7.77(d, J=8.4 Hz, 2H), 7.76(dd, J=8.7, 5.7 Hz, 2H), 7.30(t, J=8.7 Hz, 2H), 7.02(d, J=7.5 Hz, 1H), 6.85(d, J=1.2 Hz, 1H), 6.70(dd, J=7.5, 1.2 Hz, 1H), 4.18(t, J=6.3 Hz, 2H), 3.49(s, 2H), 2.94(t, J=6.3 Hz, 2H), 2.35(s, 3H), 2.05(s, 3H).

EXAMPLE 39(1)

(3-{2-[2-(3'-fluoro-1,1'-biphenyl-4-yl)-5-methyl-1,3-oxazol-4-yl]ethoxy}-4-methylphenyl)acetic acid:

TLC: Rf 0.54 (methanol:dichloromethane=1:9);

$^1$H NMR (DMSO-d$_6$): δ 12.25(brs, 1H), 7.98(d, J=8.7 Hz, 2H), 7.83(d, J=8.7 Hz, 2H), 7.62-7.44(m, 3H), 7.26-7.17(m, 1H), 7.02(d, J=7.8 Hz, 1H), 6.85(d, J=1.2 Hz, 1H), 6.70(dd, J=7.8, 1.2 Hz, 1H), 4.18(t, J=6.3 Hz, 2H), 3.49(s, 2H), 2.94(t, J=6.3 Hz, 2H), 2.36(s, 3H), 2.06(s, 3H).

EXAMPLE 39(2)

[4-methyl-3-(2-{5-methyl-2-[4-thiophen-2-yl)phenyl]-1,3-oxazol-4-yl}ethoxy)phenyl]acetic acid:
TLC: Rf 0.37 (chloroform:methanol=9:1);
$^1$H NMR (DMSO-$d_6$): δ 2.05 (s, 3H), 2.35 (s, 3H), 2.93 (t, J=6.32 Hz, 2H), 3.47 (s, 2H), 4.17 (t, J=6.32 Hz, 2H), 6.70 (dd, J=7.51, 1.28 Hz, 1H), 6.85 (dd, J=1.28, 0.73 Hz, 1H), 7.01 (dd, J=7.51, 0.73 Hz, 1H), 7.16 (dd, J=4.94, 3.66 Hz, 1H), 7.60 (dd, J=4.94, 1.10 Hz, 1H), 7.61 (dd, J=3.66, 1.10 Hz, 1H), 7.77 (d, J=8.60 Hz, 2H), 7.92 (d, J=8.60 Hz, 2H).

EXAMPLE 39(3)

[4-methyl-3-(2-{5-methyl-2-[4-(thiophen-3-yl)phenyl]-1,3-oxazol-4-yl}ethoxy)phenyl]acetic acid:
TLC: Rf 0.37 (chloroform:methanol=9:1);
$^1$H NMR (DMSO-$d_6$): δ 2.06 (s, 3H), 2.36 (s, 3H), 2.94 (t, J=6.32 Hz, 2H), 3.48 (s, 2H), 4.18 (t, J=6.32 Hz, 2H), 6.70 (dd, J=7.51, 0.92 Hz, 1H), 6.85 (d, J=0.92 Hz, 1H), 7.02 (d, J=7.51 Hz, 1H), 7.61 (dd, J=5.13, 1.46 Hz, 1H), 7.66 (dd, J=5.13, 2.93 Hz, 1H), 7.84 (d, J=8.61 Hz, 2H), 7.93 (d, J=8.61 Hz, 2H), 7.99 (dd, J=2.93, 1.46 Hz, 1H).

EXAMPLE 39(4)

[3-(2-{2-[4-(furan-2-yl)phenyl]-5-methyl-1,3-oxazol-4-yl}ethoxy)-4-methylphenyl]acetic acid:
TLC: Rf 0.33 (chloroform:methanol=9:1);
$^1$H NMR (DMSO-$d_6$): δ 2.05 (s, 3H), 2.35 (s, 3H), 2.93 (t, J=6.32 Hz, 2H), 3.48 (s, 2H), 4.18 (t, J=6.32 Hz, 2H), 6.62 (dd, J=3.48, 1.83 Hz, 1H), 6.70 (dd, J=7.69, 1.10 Hz, 1H), 6.85 (d, J=1.10 Hz, 1H), 7.02 (d, J=7.69 Hz, 1H), 7.06 (d, J=3.48 Hz, 1H), 7.80 (d, J=8.60 Hz, 2H), 7.79 (d, J=1.83 Hz, 1H), 7.94 (d, J=8.60 Hz, 2H), 12.24 (brs, 1H).

EXAMPLE 39(5)

[3-(2-{2-[4-(furan-2-yl)phenyl]-5-isopropyl-1,3-oxazol-4-yl}ethoxy)-4-methylphenyl]acetic acid:
TLC: Rf 0.35 (chloroform:methanol=9:1);
$^1$H NMR (CDCl$_3$): δ 1.33 (d, J=6.96 Hz, 6H), 2.13-2.18 (m, 3H), 3.02 (t, J=6.50 Hz, 2H), 3.15 (septet, J=6.96 Hz, 1H), 3.58 (s, 2H), 4.24 (t, J=6.50 Hz, 2H), 6.49 (dd, J=3.30, 1.83 Hz, 1H), 6.72 (d, J=3.30 Hz, 1H), 6.76 (d, J=7.51 Hz, 1H), 6.78 (s, 1H), 7.05 (d, J=7.51 Hz, 1H), 7.49 (d, J=1.83 Hz, 1H), 7.71 (d, J=8.42 Hz, 2H), 7.98 (d, J=8.42 Hz, 2H).

EXAMPLE 39(6)

[3-(2-{5-isopropyl-2-[4-(thiophen-2-yl)phenyl]-1,3-oxazol-4-yl}ethoxy)-4-methylphenyl]acetic acid:
TLC: Rf 0.35 (chloroform:methanol=9:1);
$^1$H NMR (CDCl$_3$): δ 1.33 (d, J=7.0 Hz, 6H) 2.16 (s, 3H) 3.02 (t, J=6.6 Hz, 2H) 3.15 (septet, J=7.0 Hz, 1H) 3.58 (s, 2H) 4.24 (t, J=6.6 Hz, 2H) 6.74-6.78 (m, 2H) 7.05 (d, J=7.5 Hz, 1H) 7.09 (dd, J=4.8, 3.3 Hz, 1H) 7.31 (dd, J=4.8, 1.2 Hz, 1H) 7.37 (dd, J=3.3, 1.2 Hz, 1H) 7.65 (d, J=8.7 Hz, 2H) 7.97 (d, J=8.7 Hz, 2H).

EXAMPLE 39(7)

(3-{2-[5-isopropyl-2-(4'-methoxy-1,1'-biphenyl-4-yl)-1,3-oxazol-4-yl]ethoxy}-4-methylphenyl)acetic acid:
TLC: Rf 0.41 (chloroform:methanol=9:1);
$^1$H NMR (CDCl$_3$): δ 1.32 (d, J=6.9 Hz, 6H) 2.16 (s, 3H) 3.02 (t, J=6.5 Hz, 2H) 3.15 (septet, J=6.9 Hz, 1H) 3.58 (s, 2H) 3.85 (s, 3H) 4.24 (t, J=6.5 Hz, 2H) 6.74-6.78 (m, 2H) 6.98 (d, J=6.9 Hz, 2H) 7.04 (d, J=7.5 Hz, 1H) 7.56 (d, J=6.9 Hz, 2H) 7.60 (d, J=8.7 Hz, 2H) 8.01 (d, J=8.7 Hz, 2H).

EXAMPLE 39(8)

(3-{2-[5-isopropyl-2-(4'-methyl-1,1'-biphenyl-4-yl)-1,3-oxazol-4-yl]ethoxy}-4-methylphenyl)acetic acid:
TLC: Rf 0.61 (methanol:dichloromethane=1:9);
$^1$H NMR (DMSO-$d_6$): δ 12.23(brs, 1H), 7.97(d, J=8.4 Hz, 2H), 7.76(d, J=8.4 Hz, 2H), 7.61(d, J=7.8 Hz, 2H), 7.28(d, J=7.8 Hz, 2H), 7.01(d, J=7.5 Hz, 1H), 6.87(d, J=1.2 Hz, 1H), 6.70(dd, J=7.5, 1.2 Hz, 1H), 4.21(t, J=6.3 Hz, 2H), 3.49(s, 2H), 3.19(septet, J=7.2 Hz, 1H), 2.97(t, J=6.3 Hz, 2H), 2.34(s, 3H), 2.06(s, 3H), 1.27(d, J=7.2 Hz, 6H).

BIOLOGICAL EXAMPLES

It was proved that compounds of the present invention represented by formula (I) has PPAR agonistic activities by the following experiments.

Measurement of PPAR Agonistic Activities:

(1) Preparation of materials in luciferase assay using human PPAR The measurement of present invention is the method which has advancement of the measurement accuracy and improvement of the measurement sensitivity in order to evaluate the compounds of the present invention as follows.

That is, as a luciferase gene expression vector under the control of thymidine kinase (TK) promoter, luciferase structural gene was excised from PicaGene Basic Vector 2 (trade name, Toyo Ink Inc., catalogue No. 309-04821), to prepare luciferase gene expression vector pTK-Luc. under the control of TK promoter (−105/+51) as a minimum essential promoter activity from pTKβ having TK promoter (Chrontech Inc., catalogue No. 6179-1). In the upper stream of TK promoter, four times repeated UAS sequence was inserted, which is the response sequence of Gal4 protein, a basic transcription factor in yeast, to construct 4×UAS-TK-Luc. as reporter gene. The following is the enhancer sequence used (SEQ ID NO:1).
SEQ ID NO:1: Enhancer sequence repeating Gal4 protein response sequence

5'-T(CGACGGAGTACTGTCCTCCG)×4 AGCT-3'

A vector was prepared as described hereafter which expresses chimeric receptor protein wherein in carboxyl terminus of yeast Gal4 protein DNA binding domain was fused to ligand binding domain of human PPAR α, γ or δ. That is to say, PicaGene Basic Vector 2 (trade name, Toyo Ink Inc., catalogue No. 309-04821) was used as a basic expression vector, the structural gene was exchanged for that of chimeric receptor protein, while promoter and enhancer domains were kept as they were.

DNA encoding ligand binding domain of human PPAR α, γ or δ fused to DNA encoding Gal4 protein DNA binding domain, the downstream of DNA encoding the 1st to 147th amino acid sequence for fitting their frames and inserted to the downstream of promoter/enhancer in PicaGene Basic Vector 2 (trade name, Toyo Ink Inc., catalogue No. 309-04821). Here, DNA sequence was aligned as follows, the amino terminus of human PPAR α, γ or δ ligand binding domain was sequenced nuclear translocation signal originated from SV-40 T-antigen, Ala Pro Lys Lys Lys Arg Lys Val Gly (SEQ ID NO:2), to make an expressed chimeric protein localizing intranuclearly. On the other hand, the carboxyl terminus of them was sequenced influenza hemagglutinin epitope, Tyr Pro Tyr Asp Val Pro Asp Tyr Ala (SEQ ID NO:3)

and stop codon for translation in this order, to detect an expressed fused protein tagged epitope sequence.

According to the comparison of human PPAR structures described in the literatures by R. Mukherjee et al. (See *J. Steroid Biochem. Molec. Biol.*, 51, 157 (1994)), M. E. Green et al., (See *Gene Expression.*, 4, 281 (1995)), A. Elbrecht et al. (See *Biochem Biophys. Res. Commun.*, 224, 431 (1996)) or A. Schmidt et al. (See Mol. Endocrinology., 6, 1634 (1992)), the portion of structural gene used as ligand binding domain of human PPAR α, δ or 6 was DNA encoding the following peptide:

human PPAR α ligand binding domain: $Ser^{167}$-$Tyr^{648}$
human PPAR γ ligand binding domain: $Ser^{176}$-$Tyr^{478}$
human PPAR δ ligand binding domain: $Ser^{139}$-$Tyr^{441}$ (each human PPAR γ1 ligand binding domain and human PPAR γ2 ligand binding domain is $Ser^{204}$-$Tyr^{506}$ which is identical sequence each other). In order to measure basal level of transcription, an expression vector containing DNA binding domain of Gal4 protein lacking in PPAR ligand binding domain, which is exclusively encoding the 1st to 147th amino acid sequence in Gal4 protein was also prepared.

(2) Luciferase Assay Using Human PPAR α, γ or δ

CV-1 cells used as host cells were cultured by a conventional technique. That is to say, Dulbecco's modified Eagle medium (DMEM) supplemented 10% bovine fetal serum (GIBCO BRL Inc., catalogue No. 26140-061) and 50 U/ml of penicillin G and 50 µg/ml of streptomycin sulfate were used to culture CV-1 cells under the atmosphere of 5% carbon dioxide gas at 37° C.

In case of the transfection for introducing DNA, both reporter gene and Gal-4-PPAR expression vector, into host cells, $2 \times 10^6$ cells were seeded in a 10 cm dish, and once washed with the medium without serum, followed by addition of the medium (10 ml) thereto. Reporter gene (10 µg), Gal-4-PPAR expression vector (0.5 µg) and 50 µl of LipofectAMINE (GIBRO BRL Inc., catalogue No. 18324-012) were well mixed and added to the culture dishes. They were cultured at 37° C. for 5~6 hours, and thereto was added 10 ml of medium containing 20% of dialyzed bovine fetal serum (GIBRO BRL Inc., catalogue No. 26300-061), and then cultured at 37° C. overnight. The cells were dispersed by trypsin treatment, and they were again seeded in 96-well plates in a density of 8000 cells/100 µl of DMEM-10% dialyzed serum/well. Several hours after the cultivation, when cells were attached to the plastic ware, then 100 µl of DMEM-10% dialyzed serum containing the compounds of the present invention, whose concentration is twice as high as the final concentration of them, was added thereto. The culture was settled at 37° C. for 42 hours and the cells were dissolved to measure luciferase activity according to manufacturer's instruction.

Carbacyclin activates PPAR δ, but the relative activity of the compounds of the present invention was measured under the condition that the fold increase of transcriptional activation was defined as 1 in case of final concentration 30 µM carbacyclin. And then PPAR δ fold increase of transcriptional activation of the compound prepared in Example 33 is shown in Table 1.

TABLE 1

| Final concentration (µM) | Fold increase of transcriptional activation |
|---|---|
| 0.1 | 0.47 |
| 0.3 | 1.08 |
| 1.0 | 1.23 |

As a result, the compounds of the present invention showed superior agonistic activity against PPAR δ.

Lowering Effect of Blood Cholesterol and Blood Lipid:

High cholesterol diets (CRF-1 solid pellet mixed of 5.5% peanut oil, 1.5% cholesterol, 0.5% cholic acid, Oriental Bio Service) are loaded to 7-weeks old male mice for six days and then the body weight of food-deprived rats are measured, the following various parameter levels are measured. The measurement items are LDL, HDL, TG level, NEFA, and TC level. Mice are divided into five per group based on TC level and the division was performed without bias in the average of other parameters. From the next day to six days in a row, the suspended solution of the compounds in vehicle (0.5% methylcellulose aqueous solution) are orally compellingly administered once daily and the loading of high cholesterol diets is continued. After the next day of termination of final administration (the 7th day of administration onset), plasma lipid (TG HDL, LDL, NEFA, TC level) is measured.

The relative activity of the compounds of the present invention was calculated under the condition that the value of vehicle administration group was defined as 100%. And then HDL cholesterol elevating effect and LDL cholesterol lowering effect of the compound prepared in Example 33 are shown in Table 2.

TABLE 2

| dose (mg/kg) | HDL cholesterol elevating effect | LDL cholesterol lowering effect |
|---|---|---|
| 3 | 150.0 | 82.5 |
| 10 | 162.7 | 75.7 |
| 30 | 157.3 | 72.3 |

As a result, the compound of the present invention elevated HDL depending on dose, and lowered LDL. Therefore, the compounds of the present invention are useful for therapeutic agent for hyperlipidemia.

PREPARATION EXAMPLE

Preparation Example using operation of the present invention showed below.

Preparation Example 1

The following components were admixed in a conventional method, punched out to give 10000 tablets each containing 10 mg of active ingredient.

[3-(2-{5-ethyl-2-[4-(trifluoromethoxy)phenyl]-1,3-oxazol-4-yl}ethoxy)-4-methylphenyl]acetic acid (100 g);
carboxymethylcellulosecalcium (distintegrant) (20 g);
magnesium stearate (lubricant) (10 g)
microcrystalline cellulose (870 g).

Preparation Example 2

After mixing the following components by a conventional method, the resulting solution was filtrated by dust-proof filter and 5 ml portions thereof were filled in ampuls, respectively, and heat-sterilized by autoclave to obtain 10000 ampuls of injection containing each 20 mg of the active ingredient.

[3-(2-{5-ethyl-2-[4-(trifluoromethoxy)phenyl]-1,3-oxazol-4-yl}ethoxy)-4-methylphenyl]acetic acid (200 g);

mannitol (2 kg);
distilled water (50 L).

INDUSTRIAL AVAILABILITY

Toxicity of the compound represented by formula (I), a salt thereof or a solvent thereof, or a prodrug thereof is very low, and it is safe enough to use as a pharmaceutical agent. In addition, since it is PPAR agonist, it is useful as preventive and/or therapeutic agent for hyperlipidemia etc.

$R^3$ represents C1-8 alkyl which may be substituted with a 1-3 halogen atom(s) or phenyl;

$R^4$ represents a hydrogen atom or C1-8 alkyl;

$R^5$ and $R^6$ each independently represents a hydrogen atom or C1-4 alkyl, or $R^5$ and $R^6$ may be together with their neighboring carbon atom to form a carbocyclic ring;

X represents a sulfur atom, an oxygen atom or a nitrogen atom which may have a substituent(s);

---

---

The invention claimed is:

1. A compound represented by formula (I)

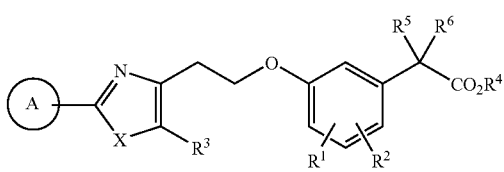

wherein $R^1$ and $R^2$ each independently represents a hydrogen atom, C1-8 alkyl, a halogen atom, C1-4 alkoxy, nitro, trihalomethyl, trihalomethoxy, trihalomethylthio, cyano, C1-4 alkylthio or $NR^7R^8$, in which $R^7$ and $R^8$ each independently represents a hydrogen atom or C1-4 alkyl;

ring A represents 4-(trifluoromethyl)piperidin-1-yl or 3,4-dihydro-1H-isoquinolin-2-yl, or a salt thereof.

2. The compound according to claim 1, wherein the compound is (1) [3-(2-{5-methyl-2-[4-(trifluoromethyl)piperidin-1-yl]-1,3-thiazol-4-yl}ethoxy)phenyl]acetic acid, (2) [3-(2-{5-ethyl-2-[4-(trifluoromethyl)piperidin-1-yl]-1,3-thiazol-4-yl}ethoxy)-4-methylphenyl]acetic acid, (3) [2-fluoro-3-(2-{5-methyl-2-[4-(trifluoromethyl)piperidin-1-yl]-1,3-thiazol-4-yl}ethoxy)phenyl]acetic acid, or (4) (3-{2-[2-(3,4-dihydro-1H-isoquinolin-2-yl)-5-methyl-1,3-thiazol-4-yl]ethoxy}-4-methylphenyl)acetic acid.

3. A pharmaceutical composition comprising the compound represented by formula (I) according to claim 1, or a salt thereof, and a pharmaceutically acceptable carrier.

4. The pharmaceutical composition according to claim 3, wherein the pharmaceutical composition is a therapeutic agent for hyperlipidemia or adiposity.

5. A pharmaceutical composition comprising the compound represented by formula (I) according to claim 1, or a salt thereof and one or more components selected from the group consisting of a MTP inhibitor, a HMG-CoA reductase inhibitor, a squalene synthase inhibitor, a fibrate drug, an ACAT inhibitor, a 5-lipoxygenase inhibitor, a cholesterol absorption inhibitor, a bile acid absorption inhibitor, a $Na^+$/bile acid transporter inhibitor, LDL receptor activator, LDL receptor expression enhancer, a pancreatic lipase inhibitor, a probucol formulation, a nicotine acid formulation and a cholesterol ester transporter protein inhibitor.

6. A method for treatment of hyperlipidemia or adiposity in a mammal, which comprises administering to a mammal an effective amount of a compound selected from the group consisting of
(1) (3-{2-[2-(3,4-dihydro-1H-isoquinolin-2-yl)-5-methyl-1,3-thiazol-4-yl]ethoxy}-4-methylphenyl)acetic acid,
(2) [2-fluoro-3-(2-{5-methyl-2-[4-(trifluoromethyl)piperidin-1-yl]-1,3-thiazol-4-yl}ethoxy)phenyl]acetic acid, and
(3) (3-{2-[2-(2,2-difluoro-1,3-benzodioxol-5-yl)-5-isopropyl-1,3-oxazol-4-yl]ethoxy}-4-methylphenyl)acetic acid
or a salt thereof.

7. A compound selected from a group consisting of
(1) (3-{2-[2-(3,4-dihydro-1H-isoquinolin-2-yl)-5-methyl-1,3-thiazol-4-yl]ethoxy}-4-methylphenyl)acetic acid and
(2) [2-fluoro-3-(2-{5-methyl-2-[4-(trifluoromethyl)piperidin-1-yl]-1,3-thiazol-4-yl }ethoxy)phenyl]acetic acid.

8. A compound of (3-{2-[2-(2,2-difluoro-1,3-benzodioxol-5-yl)-5-isopropyl-1,3-oxazol-4-yl]ethoxy}-4-methylphenyl)acetic acid.

* * * * *

SEQUENCE LISTING

<160> NUMBER OF SEQ ID NOS: 3

<210> SEQ ID NO 1
<211> LENGTH: 85
<212> TYPE: DNA
<213> ORGANISM: Artificial Sequence
<220> FEATURE:
<223> OTHER INFORMATION: Chemically synthesized enhancer sequence
      including 4 times repeated Gal4 protein response sequences

<400> SEQUENCE: 1
tcgacggagt actgtcctcc gcgacggagt actgtcctcc gcgacggagt actgtcctcc      60
gcgacggagt actgtcctcc gagct                                            85

<210> SEQ ID NO 2
<211> LENGTH: 9
<212> TYPE: PRT
<213> ORGANISM: Simian virus 40

<400> SEQUENCE: 2

Ala Pro Lys Lys Lys Arg Lys Val Gly
1               5

<210> SEQ ID NO 3
<211> LENGTH: 9
<212> TYPE: PRT
<213> ORGANISM: Influenza virus

<400> SEQUENCE: 3

Tyr Pro Tyr Asp Val Pro Asp Tyr Ala
1               5